(12) United States Patent
Michellys et al.

(10) Patent No.: US 7,807,841 B2
(45) Date of Patent: Oct. 5, 2010

(54) SPIRO-CONTAINING COMPOUNDS AND COMPOSITIONS AS MODULATORS OF STEROID HORMONE NUCLEAR RECEPTORS

(75) Inventors: Pierre-Yves Michellys, San Marcos, CA (US); Chi Ching Mak, San Diego, CA (US); Wei Pei, San Diego, CA (US)

(73) Assignee: IRM LLC, Hamilton (BM)

( * ) Notice: Subject to any disclaimer, the term of this patent is extended or adjusted under 35 U.S.C. 154(b) by 175 days.

(21) Appl. No.: 11/816,097

(22) PCT Filed: Feb. 16, 2006

(86) PCT No.: PCT/US2006/005803

§ 371 (c)(1),
(2), (4) Date: Apr. 3, 2008

(87) PCT Pub. No.: WO2006/104594

PCT Pub. Date: Oct. 5, 2006

(65) Prior Publication Data

US 2009/0124597 A1    May 14, 2009

Related U.S. Application Data

(60) Provisional application No. 60/656,861, filed on Feb. 25, 2005.

(51) Int. Cl.
*C07D 413/00* (2006.01)
*C07D 263/00* (2006.01)

(52) U.S. Cl. .................. 548/215; 548/216; 548/225

(58) Field of Classification Search ................. 548/215, 548/216, 225
See application file for complete search history.

(56) References Cited

U.S. PATENT DOCUMENTS 3,138,608 A * 6/1964 Davis .................... 548/216
6,777,410 B2   8/2004 Nagase et al.

FOREIGN PATENT DOCUMENTS

| EP | 0456183 | 11/1991 |
|---|---|---|
| WO | WO03078394 | 9/2003 |
| WO | WO2004052847 | 6/2004 |

OTHER PUBLICATIONS

Andrews et al., Chemical Communications, vol. 3, 1999, 249-250, especially p. 249.*
Morisette, et al., Advanced Drug Delivery Review, vol. 56, 2004, pp. 275-300, especially p. 275.*
Andrews, et al., Chem. Comm., 1999, vol. 3, 249-250.*
International Search Report-Mailed Sep. 25, 2007.
International Preliminar Report on Patentability-Mailed Oct. 25, 2007.

* cited by examiner

*Primary Examiner*—Susannah Chung
(74) *Attorney, Agent, or Firm*—Daniel E. Raymond; Genomics Institute of the Novartis Research Foundation

(57) ABSTRACT

Described herein are compounds that have a spiro structural feature. Also described herein are methods for making such compounds, methods for using such compounds to modulate the activity of steroid hormone nuclear receptors, and pharmaceutical compositions and medicaments comprising such compounds. Also described herein are methods of using such compounds, pharmaceutical compositions and medicaments to treat and/or prevent diseases or conditions associated with the activity of steroid hormone nuclear receptors.

23 Claims, No Drawings

SPIRO-CONTAINING COMPOUNDS AND COMPOSITIONS AS MODULATORS OF STEROID HORMONE NUCLEAR RECEPTORS

This application is a 371 U.S. national phase application of international application number PCT/US2006/005803 filed 16 Feb. 2006, which application claims priority to U.S. Provisional Patent Application No. 60/656,861, filed 25 Feb. 2005. The full disclosure of these applications is incorporated herein by reference in its entirety and for all purposes.

FIELD OF THE INVENTION

Compounds, methods of making such compounds, pharmaceutical compositions and medicaments comprising such compounds, and methods of using such compounds to treat or prevent diseases or conditions associated with the activation of steroid hormone nuclear receptors are described

BACKGROUND OF THE INVENTION

Steroid hormone nuclear receptors represent a subset of the nuclear hormone receptor superfamily. So named according to the cognate ligand which complexes with the receptor in its native state, the steroid hormone nuclear receptors include the glucocorticoid receptor (GR), the androgen receptor (AR), the mineralocorticoid receptor (MR), the estrogen receptor (ER), and the progesterone receptor (PR). MR is expressed in epithelial tissues, heart, kidneys, brain, vascular tissues and bone. Aldosterone is the endogenous ligand of MR and is primarily synthesized in the adrenal glands, heart, brain and blood vessels. Several detrimental effects are attributable to aldosterone, for example: sodium/water retention, renal fibrosis, vascular inflammation, vascular fibrosis, endothelial dysfunction, coronary inflammation, decrease in coronary blood flow, ventricular arrhythmias, myocardial fibrosis, ventricular hypertrophy and direct damage to cardiovascular systems, primarily the heart, vasculature and kidneys. Aldosterone action on all target organs is through activation of the MR receptor. GR is expressed in almost all tissues and organ systems and is crucial for the integrity of the function of the central nervous system and the maintenance of cardiovascular, metabolic, and immune homeostasis.

SUMMARY OF THE INVENTION

In one aspect are compounds having a spiro structure. In another aspect is the use of such compounds having a spiro structure for the modulation of a nuclear receptor. In another aspect is the use of such compounds having a spiro structure in the treatment of a disease or condition, or to produce a medicament for the treatment of a disease or condition, in which modulation of at least one nuclear receptor activity can prevent, inhibit or ameliorate the pathology and/or symptoms of the disease or condition. In another aspect are pharmaceutical compositions comprising such a compound having a spiro structure. In another aspect are methods for making such compounds having a spiro structure.

In one aspect are compounds having the structure of Formula (A):

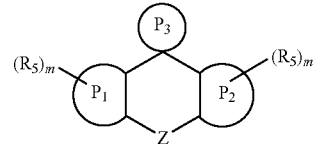

(A)

wherein the ring structures of $P_1$ and $P_2$ are independently selected from optionally substituted cycloalkyl, heterocycloalkyl, aryl, and heteroaryl, wherein each optional substituent $R_5$ is independently selected from halogen, OH, $NH_2$, SH, $NO_2$, CN, and an optionally substituted moiety selected from -$L_2$-alkyl, -$L_2$-cycloalkyl, -$L_2$-heteroalkyl, -$L_2$-haloalkyl, -$L_2$-aryl, -$L_2$-heterocycloalkyl, or -$L_2$-heteroaryl, wherein $L_2$ is selected from a bond, O, NH, S, —C(O)—, —C(S)—, —C(O)O—, —C(O)NH—, —S(O)—, —S(O)$_2$, —S(O)NH—, and wherein each m is independently selected from 0, 1, 2, 3, 4, 5, and 6; the ring structure $P_3$ is a spiro structure comprised of 5, 6, 7, or 8 atoms, wherein at least one of the atoms of $P_3$ is a heteroatom, X, selected from O, $NR_7$, $C(R_8)_2$, and S, and Z is $CR_6$=$CR_6$ or $C(R_6)_2$—$C(R_6)_2$.

In one aspect are compounds having the structure of Formula (1):

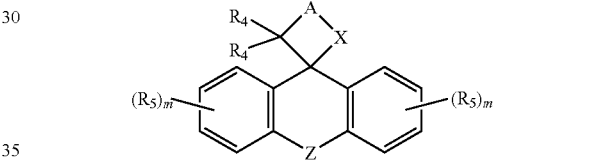

(1)

wherein, (a) A is $NR_1$—$CR_2R_3$ or N=$CR_2$; X is O, $NR_7$, $C(R_9)_2$, or S; Z is $CR_6$=$CR_6$ or $C(R_6)_2$—$C(R_6)_2$; (b) $R_1$ is H, or an optionally substituted moiety selected from -$L_1$-alkyl, -$L_1$-cycloalkyl, -$L_1$-heteroalkyl, -$L_1$-haloalkyl, -$L_1$-aryl, -$L_1$-heterocycloalkyl, and -$L_1$-heteroaryl, wherein $L_1$ is selected from a bond, —C(O)—, —C(S)—, —C(O)O—, —C(O)NH—, —S(O)—, —S(O)$_2$, and —S(O)NH—; wherein said optional substituents of an $R_1$ moiety are selected from halogen, OH, $C_{1-6}$alkyl, $C_{1-6}$alkoxy, halo-$C_{1-6}$alkyl and halo-$C_{1-6}$alkoxy; $R_2$ and $R_3$ are independently selected from H, halogen, OH, $NH_2$, SH, $NO_2$, CN, and an optionally substituted moiety selected from -$L_2$-alkyl, -$L_2$-cycloalkyl, -$L_2$-heteroalkyl, -$L_2$-haloalkyl, -$L_2$-aryl, -$L_2$-heterocycloalkyl, and -$L_2$-heteroaryl, wherein $L_2$ is selected from a bond, O, NH, S, —C(O)—, —C(S)—, —C(O)O—, —C(O)NH—, —S(O)—, —S(O)$_2$, and —S(O)NH—; wherein said optional substituents of an $R_2$ or $R_3$ moiety are selected from halogen, OH, $C_{1-6}$alkyl, $C_{1-6}$alkoxy, halo-$C_{1-6}$alkyl and halo-$C_{1-6}$alkoxy; or $R_1$ and $R_2$ together form an optionally substituted 3 to 8-membered heterocyclic ring; or $R_2$ and $R_3$ together form an optionally substituted 3 to 8-membered cycloalkyl, carbocyclic or heterocyclic ring; (c) each $R_4$ is independently selected from H, halogen, OH, $NH_2$, SH, $NO_2$, CN, and an optionally substituted moiety selected from -$L_2$-alkyl, -$L_2$-cycloalkyl, -$L_2$-heteroalkyl, -$L_2$-haloalkyl, -$L_2$-aryl, -$L_2$-heterocycloalkyl, and -$L_2$-heteroaryl, wherein $L_2$ is selected from a bond, O, NH, S, —C(O)—, —C(S)—, —C(O)O—, —C(O)NH—, —S(O)—, —S(O)$_2$, and —S(O)NH—, provided that at least one $R_4$ is not H; (d) each $R_5$ is independently selected from halogen, OH, $NH_2$, SH, $NO_2$, CN, and an optionally substituted moiety selected from -L$_2$-alkyl, -L$_2$-cycloalkyl, -L$_2$-heteroalkyl, -L$_2$-haloalkyl, -L$_2$-aryl, -L$_2$-heterocycloalkyl, and -L$_2$-heteroaryl, wherein L$_2$ is selected from a bond, O, NH, S, —C(O)—, —C(S)—, —C(O)O—, —C(O)NH—, —S(O)—, —S(O)$_2$, and —S(O)NH—, and wherein each m is independently selected from 0, 1, 2, 3, 4, and 5; (e) each R$_6$ is independently selected from H, halogen, OH, NH$_2$, SH, NO$_2$, CN, and an optionally substituted moiety selected from -L$_2$-alkyl, -L$_2$-cycloalkyl, -L$_2$-heteroalkyl, -L$_2$-haloalkyl, -L$_2$-aryl, -L$_2$-heterocycloalkyl, and -L$_2$-heteroaryl, wherein L$_2$ is selected from a bond, O, NH, S, —C(O)—, —C(S)—, —C(O)O—, —C(O)NH—, —S(O)—, —S(O)$_2$, and —S(O)NH—, or any two R$_6$ groups can together form a 3 to 8-membered carbocyclic or heterocyclic ring; and (f) each R$_7$ and R$_9$ is independently selected from H and (C$_1$-C$_4$)alkyl; and a pharmaceutically acceptable salt, pharmaceutically acceptable N-oxide, pharmaceutically active metabolite, pharmaceutically acceptable prodrug, or pharmaceutically acceptable solvate thereof.

In an embodiment of the aforementioned aspect X is O. In a further or alternative embodiment of this aspect X is O and Z is CR$_6$═CR$_6$. In a further or alternative embodiment of this aspect X is O and Z is C(R$_6$)$_2$—C(R$_6$)$_2$. In a further or alternative embodiment of this aspect A is NR$_1$—CR$_2$R$_3$. In a further or alternative embodiment of this aspect A is NR$_1$—CR$_2$R$_3$, and X is O. In a further or alternative embodiment of this aspect A is NR$_1$—CR$_2$R$_3$, X is O, and Z is CR$_6$═CR$_6$. In a further or alternative embodiment of this aspect A is NR$_1$—CR$_2$R$_3$, X is O, and wherein Z is C(R$_6$)$_2$—C(R$_6$)$_2$. In a further or alternative embodiment of this aspect A is NR$_1$—CR$_2$R$_3$, X is O, and R$_1$ and R$_2$ together form a 3 to 8-membered heterocyclic ring. In a further or alternative embodiment of this aspect A is NR$_1$—CR$_2$R$_3$, X is O, Z is CR$_6$═CR$_6$, and R$_1$ and R$_2$ together form a 3 to 8-membered heterocyclic ring. In a further or alternative embodiment of this aspect A is NR$_1$—CR$_2$R$_3$, X is O, Z is C(R$_6$)$_2$—C(R$_6$)$_2$, and R$_1$ and R$_2$ together form a 3 to 8-membered heterocyclic ring.

In a further or alternative embodiment of this aspect, A is NR$_1$—CR$_2$R$_3$, and R$_2$ and R$_3$ together form an optionally substituted 3 to 8-membered carbocyclic or heterocyclic ring. In a further or alternative embodiment, X is O. In a further or alternative embodiment, Z is CR$_6$═CR$_6$. In a further or alternative embodiment, Z is C(R$_6$)$_2$—C(R$_6$)$_2$. In a further or alternative embodiment, R$_1$ is not H.

In a further or alternative embodiment of this aspect, A is N═CR$_2$. In a further or alternative embodiment, X is O. In a further or alternative embodiment, Z is CR$_6$═CR$_6$. In a further or alternative embodiment, Z is C(R$_6$)$_2$—C(R$_6$)$_2$.

In a further or alternative embodiment of this aspect A is NR$_1$—CR$_2$R$_3$ and R$_1$ is not H. In a further or alternative embodiment of this aspect A is NR$_1$—CR$_2$R$_3$ and R$_1$ and R$_2$ together form a 3 to 8-membered heterocyclic ring. In a further or alternative embodiment of this aspect A is NR$_1$—CR$_2$R$_3$, and X is O. In a further or alternative embodiment of this aspect A is NR$_1$—CR$_2$R$_3$, X is O, and Z is CR$_6$═CR$_6$. In a further or alternative embodiment of this aspect A is NR$_1$—CR$_2$R$_3$, X is O, and Z is C(R$_6$)$_2$—C(R$_6$)$_2$.

In a further or alternative embodiment of this aspect A is NR$_1$—CR$_2$R$_3$, and R$_2$ and R$_3$ together form an optionally substituted 3 to 8-membered carbocyclic or heterocyclic ring. In a further or alternative embodiment, X is O. In a further or alternative embodiment, Z is CR$_6$═CR$_6$. In a further or alternative embodiment, Z is C(R$_6$)$_2$—C(R$_6$)$_2$. In a further or alternative embodiment, R$_1$ is not H.

In another aspect are compounds having the structure of Formula (2):

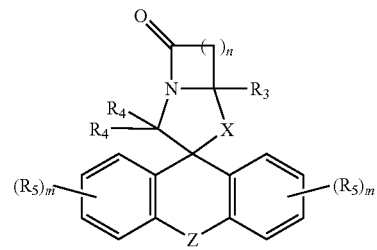

wherein n is 0, 1, 2, 3, 4 or 5.

In an embodiment of the aforementioned aspect X is O. In a further or alternative embodiment of this aspect X is O and Z is CR$_6$═CR$_6$. In a further or alternative embodiment of this aspect X is O and Z is C(R$_6$)$_2$—C(R$_6$)$_2$.

In another aspect are methods for modulating the activity of at least one steroid hormone nuclear receptor comprising contacting at least one steroid hormone nuclear receptor with a compound having the structure of Formula (1), or a pharmaceutically acceptable salt, pharmaceutically acceptable N-oxide, pharmaceutically active metabolite, pharmaceutically acceptable prodrug, or pharmaceutically acceptable solvate thereof.

In a further or alternative embodiment of this aspect, the compound directly contacts at least one steroid hormone nuclear receptor. In a further or alternative embodiment, the contacting occurs in vitro. In a further or alternative embodiment, the contacting occurs in vivo.

In another aspect are pharmaceutical compositions comprising at least one compound having the structure of Formula (1), or a pharmaceutically acceptable salt, pharmaceutically acceptable N-oxide, pharmaceutically active metabolite, pharmaceutically acceptable prodrug, or pharmaceutically acceptable solvate thereof, in admixture with one or more suitable excipients. In a further or alternative embodiment, the one or more excipients are suitable for parenteral administration. In a further or alternative embodiment, the one or more excipients are suitable for oral administration. In a further or alternative embodiment, the one or more excipients are suitable for ophthalmic administration.

In another aspect are methods of treating a disease or condition in an animal in which modulation of steroid hormone nuclear receptor activities can prevent, inhibit or ameliorate the pathology and/or symptoms of the disease or condition, which method comprises administering to the animal a therapeutically effective amount of a compound of Formula (1), or a pharmaceutically acceptable salt, pharmaceutically acceptable N-oxide, pharmaceutically active metabolite, pharmaceutically acceptable prodrug, or pharmaceutically acceptable solvate thereof. In a further or alternative embodiment, the steroid hormone nuclear receptor is selected from the group consisting of a glucocorticoid receptor, a mineralocorticoid receptor, an androgen receptor, an estrogen receptor, and a progesterone receptor.

In a further or alternative embodiment, the method further comprises administration of a therapeutically effective amount of second substance, wherein the second substance is used in the treatment of a disease or condition selected from the group consisting of hypokalemia, hypertension, congestive heart failure, renal failure, in particular chronic renal failure, restenosis, atherosclerosis, syndrome X, obesity, nephropathy, post-myocardial infarction, coronary heart disease, increased formation of collagen, fibrosis and remodeling following hypertension and endothelial dysfunction. In a further or alternative embodiment, the substance is selected from the group consisting of an anti-obesity agent, an anti-hypertensive agent, an inotropic agent, an hypolipidemic agent, an angiotensin converting enzyme (ACE) inhibitor, an inhibitor of the Na-K-ATPase membrane pump, an neutral-endopeptidase (NEP) inhibitor, an ACE/NEP inhibitor, an angiotensin II antagonist, a β-adrenergic receptor blocker, an inotropic agent, a calcium channel blocker, and a 3-hydroxy-3-methyl-glutaryl coenzyme A reductase (HMG-CoA) inhibitor. In a further or alternative embodiment, the compound of Formula (1) is administered prior to the second substance. In a further or alternative embodiment, the compound of Formula (1) is administered with the second substance. In a further or alternative embodiment, the compound of Formula (1) is administered after the second substance.

In another aspect is the use of a compound of Formula (1) in the manufacture of a medicament for treating a disease or condition in an animal in which steroid hormone nuclear receptor activity contributes to the pathology and/or symptoms of the disease or condition. In a further or alternative embodiment, the steroid hormone nuclear receptor is selected from the group consisting of a glucocorticoid receptor, a mineralocorticoid receptor, an androgen receptor, an estrogen receptor, and a progesterone receptor.

In another aspect are methods for preparing a compound having the structure of Formula (2):

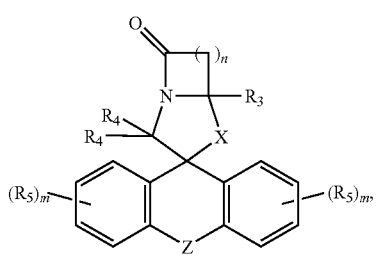

(2)

comprising admixing a ketoacid compound with a compound having the structure of Formula (3):

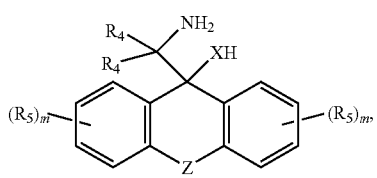

(3)

under suitable reaction conditions. In a further or alternative embodiment, X is O.

In another aspect are methods for preparing a compound having the structure of Formula (4):

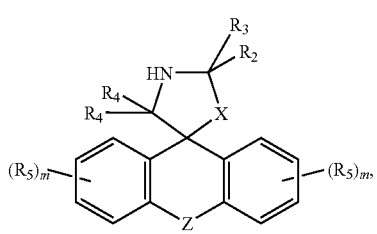

(4)

comprising admixing a ketone with a compound having the structure of Formula (3):

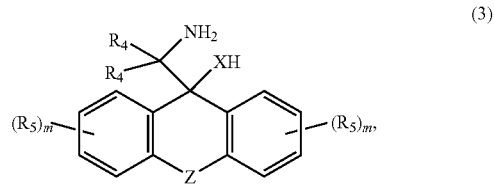

(3)

under suitable reaction conditions. In a further or alternative embodiment, X is O.

In another aspect are methods for preparing a compound having the structure of Formula (5):

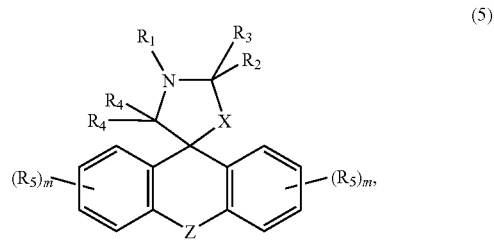

(5)

comprising admixing an electrophilic reactant with a compound having the structure of Formula (4):

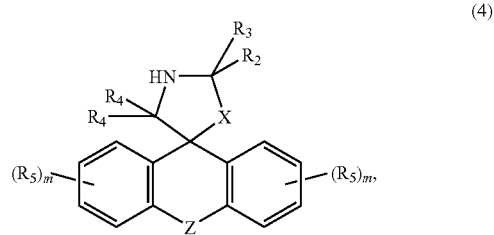

(4)

under suitable reaction conditions. In a further embodiment, the electrophilic reactant is selected from an acid chloride, an anhydride, an isocyanate, an isothiocyanate, or a sulfonyl chloride. In a further or alternative embodiment, X is O.

In another aspect are methods for preparing a compound having the structure of Formula (6):

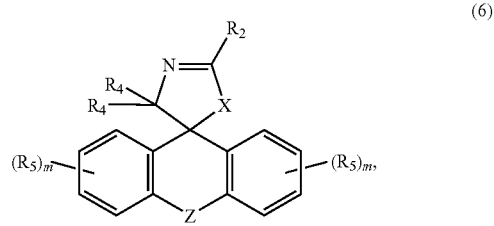

(6)

comprising admixing an imidate compound with a compound having the structure of Formula (3):

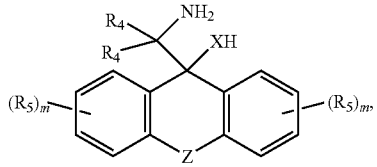

under suitable reaction conditions. In a further embodiment, X is O.

Although the orientation of spiro-compounds described herein appears with certain functional groups in one orientation, this structural depiction should be considered identical, unless explicitly stated otherwise, to the mirror image orientation. By way of example only, below;

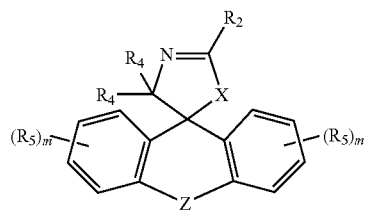

is equivalent to

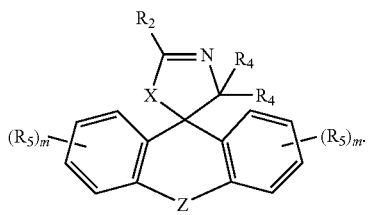

Therefore, unless stated otherwise both orientations of the spiro- groups should be considered identical representations for all purposes described herein.

For convenience, all of the aspects and embodiments described in this section and other parts herein use a single formula, such as "Formula (1)," by way of example. However, all of the aspects and embodiments described herein apply equally well to all formulas presented herein that fall within the scope of Formula (A). For example, all of the aspects and embodiments described herein can be applied to compounds having the structure of Formula (B), Formula (C), Formula (E), Formula (F), Formula (G), Formula (H), Formula (I), Formula (J), Formula (K), Formula (A), Formula (2), Formula (4), Formula (5), Formula (6), as well as to all of the specific compounds that fall within the scope of these generic formula.

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the invention will become apparent to those skilled in the art from this detailed description.

These and other aspects of the present invention will become evident upon reference to the following detailed description. In addition, all patents and other references cited herein which describe in more detail certain procedures or compositions, and are incorporated by reference in their entirety.

DETAILED DESCRIPTION OF THE INVENTION

Certain Chemical Terminology

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg "ADVANCED ORGANIC CHEMISTRY $4^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the skill of the art are employed.

The term "alkenyl group", as used herein, refers to a hydrocarbon chain having one or more double bonds therein. The double bond of an alkenyl group can be unconjugated or conjugated to another unsaturated group. Suitable alkenyl groups include, but are not limited to, $(C_2-C_8)$alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. The alkenyl moiety may be branched, straight chain, or cyclic (in which case, it would also be known as a "cycloalkenyl" group), and can be unsubstituted or substituted.

The term "alkoxy" as used herein, includes —O-(alkyl), where alkyl is as defined herein. By way of example only, $C_{1-6}$ alkoxy includes, but is not limited to, methoxy, ethoxy, and the like. An alkoxy group can be unsubstituted or substituted.

The term "alkyl", as used herein, refers to a hydrocarbon group having from 1 to 10 carbon atoms and can include straight, branched, cyclic, saturated and/or unsaturated features. Whenever it appears herein, a numerical range such as "1 to 10" refers to each integer in the given range; e.g., "1 to 10 carbon atoms" or "$C_{1-10}$" or "$(C_1-C_{10})$" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated. The alkyl moiety may be a "saturated alkyl" group, which means that it does not contain any alkene or alkyne moieties. Representative saturated alkyl groups include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, sec-butyl, t-butyl, n-pentyl, isopentyl, neopentyl, and n-hexyl, and longer alkyl groups, such as heptyl, and octyl. The alkyl moiety may also be an "unsaturated alkyl" moiety, which means that it contains at least one alkene or alkyne moiety. An "alkene" moiety refers to a group consisting of at least two carbon atoms and at least one carbon-carbon double bond, and an "alkyne" moiety refers to a group consisting of at least two carbon atoms and at least one carbon-carbon triple bond. Representative unsaturated alkyl groups include, but are not limited to, ethenyl, propenyl, butenyl and the like. An alkyl group can be unsubstituted or substituted. Substituted alkyl groups include, but are not limited to, halogen-substituted alkyl groups, such as, by way of example only, trifluoromethyl, pentafluoroethyl, and the like.

The term "alkylamine", as used herein, refers to the —N(alkyl)$_x$H$_y$ group, where x and y are selected from the group x=1, y=1 and x=2, y=0. When x=2, the alkyl groups, taken together, can optionally form a cyclic ring system and further when x=2, the alkyl groups can be the same or different. An alkylamine group can be unsubstituted or substituted.

The term "alkynyl" group, as used herein, refers to a hydrocarbon chain having one or more triple bonds therein. The triple bond of an alkynyl group can be unconjugated or conjugated to another unsaturated group. Suitable alkynyl groups include, but are not limited to, ($C_2$-$C_6$)alkynyl groups, such as ethynyl, propynyl, butynyl, pentynyl, hexynyl, methylpropynyl, 4-methyl-1-butynyl, 4-propyl-2-pentynyl, and 4-butyl-2-hexynyl. The alkynyl moiety may be branched or straight chain, and can be unsubstituted or substituted.

The term "amide", as used herein, refers to a chemical moiety with formula —C(O)NHR or —NHC(O)R, where R is selected from the group consisting of alkyl, cycloalkyl, aryl, and heterocyclic (bonded through a ring carbon). Amides can be formed from any amine or carboxyl side chain on the compounds described herein. The procedures and specific groups to make such amides are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein by reference in its entirety. An amide group can be unsubstituted or substituted.

The term "aromatic" or "aryl", as used herein, refers to a closed ring structure which has at least one ring having a conjugated pi electron system and includes both carbocyclic aryl and heterocyclic aryl (or "heteroaryl" or "heteroaromatic") groups. The carbocyclic or heterocyclic aromatic group may contain from 5 to 20 ring atoms. The term includes monocyclic or fused-ring polycyclic (i.e., rings which share adjacent pairs of carbon atoms) groups. An aromatic group can be unsubstituted or substituted.

The term "aryloxy", as used herein, includes —O-aryl group, wherein aryl is as defined herein. An aryloxy group can be unsubstituted or substituted.

The term "bond" or "single bond", as used herein, refers to a covalent bond between two atoms, either of which may be part of a larger moiety.

The terms "carbocyclic" or "cycloalkyl", as used herein, refer to a compound which contains one or more covalently closed ring structures, and that the atoms forming the backbone of the ring are all carbon atoms. Such a group may have from 3 to 20 ring carbon atoms and be saturated, partially unsaturated, or fully unsaturated monocyclic, fused bicyclic, spirocyclic, bridged polycyclic or polycyclic ring comprising carbon and hydrogen atoms. Carbocyclic alkyl groups include, but are not limited to, cyclopropyl, cyclobutyl, cyclopentyl, cyclohexyl, cycloheptyl, and cyclooctyl. A carbocyclic aromatic group includes, but is not limited to, phenyl, tolyl, anthracenyl, fluorenyl, indenyl, azulenyl, and naphthyl, as well as benzo-fused carbocyclic moieties such as, by way of example only, dibenzosuberenone, and dibenzosuberone. A carbocyclic group can be unsubstituted or substituted.

The term "ester", as used herein, refers to a chemical moiety with formula —COOR, where R is selected from the group consisting of alkyl, cycloalkyl, aryl, and heterocyclic (bonded through a ring carbon). Any hydroxy or carboxyl side chain on the compounds described herein can be esterified. The procedures and specific groups to make such esters are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein by reference in its entirety. An ester group can be unsubstituted or substituted.

The terms "heteroalkyl" "heteroalkenyl" and "heteroalkynyl", as used herein, include optionally substituted alkyl, alkenyl and alkynyl moieties and which have one or more skeletal chain atoms selected from an atom other than carbon, e.g., oxygen, nitrogen, sulfur, phosphorus or combinations thereof. A "heteroalkyl" "heteroalkenyl" and "heteroalkynyl" group can be unsubstituted or substituted.

The terms "heteroaryl" or, alternatively, "heteroaromatic", as used herein, refers to an aryl group that includes one or more ring heteroatoms selected from nitrogen, oxygen, sulfur. By way of example, an N-containing "heteroaromatic" or "heteroaryl" moiety refers to an aromatic group in which at least one of the skeletal atoms of the ring is a nitrogen atom. A polycyclic heteroaryl group may be fused or non-fused. A heteroaryl group can be unsubstituted or substituted.

The term "heterocyclic", as used herein, refers to ring structures in which the ring backbone contains at least one atom selected from nitrogen, oxygen, and sulfur. Examples of heterocyclic aromatic groups include, but are not limited to, acridinyl, benzo[1,3]dioxole, benzimidazolyl, benzindazolyl, benzoisooxazolyl, benzokisazolyl, benzofuranyl, benzofurazanyl, benzopyranyl, benzothiazolyl, benzo[b]thienyl, benzothiophenyl, benzothiopyranyl, benzotriazolyl, benzoxazolyl, carbazolyl, carbolinyl, cinnolinyl, furanyl, furazanyl, furopyridinyl, furyl, imidazolyl, indazolyl, indolyl, indolidinyl, indolizinyl, isobenzofuranyl, isoindolyl, isoxazolyl, isoquinolinyl, isothiazolyl, naphthylidinyl, naphthyridinyl, oxadiazolyl, oxazolyl, phenoxazinyl, phenothiazinyl, phenazinyl, phenoxathilynyl, thianthrenyl, phenanthridinyl, phenathrolinyl, phthalazinyl, pteridinyl, purinyl, puteridinyl, pyrazyl, pyrazolyl, pyridyl, pyridinyl, pyridazinyl, pyrazinyl, pyrimidinyl, pyrimidyl, pyrrolyl, quinazolinyl, quinolinyl, quinoxalinyl, tetrazolyl, thiadiazolyl, thiazolyl, thienyl, triazinyl, (1,2,3,)- and (1,2,4)-triazolyl and the like. In addition, a heterocyclic group can be unsubstituted or substituted. Examples of non-aromatic heterocyclic groups include, but are not limited to, are azepinyl, azepan-2-Onyl, azetidinyl, diazepinyl, dihydrofuranyl, dihydropyranyl, dihydrothienyl, dioxanyl, dioxolanyl, 1,4-dioxa-8-aza-spiro[4.5]dec-8-yl, dithianyl, dithiolanyl, homopiperidinyl, imidazolinyl, imidazolidinyl, indolinyl, indolyl, morpholinyl, oxazepinyl, oxepanyl, oxetanyl, oxylanyl, piperidino, piperidyl, piperidinonyl, piperazinyl, pyranyl, pyrazolinyl, pyrazolidinyl, pyrrolidinyl, pyrrolidinonyl, pyrrolinyl, quinolizinyl, thietanyl, tetrahydrofuranyl, tetrahydroquinolyl, tetrahydrothienyl, tetrahydrothiopyranyl, tetrahydropyridinyl, tetrahydropyranyl, thiazepinyl, thiepanyl, thiomorpholinyl, thioranyl, thioxanyl and the like. The heterocyclic group may be fused or non-fused. The terms referring to the groups also encompass all possible tautomers.

The term "halogen", as used herein, means fluoro, chloro, bromo or iodo. Preferred halogen groups are fluoro, chloro and bromo.

The terms "haloalkyl," "haloalkenyl," "haloalkynyl" and "haloalkoxy" include alkyl, alkenyl, alkynyl and alkoxy structures that are substituted with one or more halogen groups or with combinations thereof.

The term "membered ring", as used herein, can embrace any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

The term "moiety", as used herein, refers to a specific segment or functional group of a molecule. Chemical moieties are often recognized chemical entities embedded in or appended to a molecule.

The term "protecting group", as used herein, refers to a chemical moiety which blocks some or all reactive moieties and prevent such groups from participating in chemical reactions until the protective group is removed.

The term "reactant", as used herein, refers to a nucleophile or electrophile used to create covalent linkages.

The term "sulfonyl" refers to the presence of a sulfur atom, which is optionally linked to another moiety such as an alkyl group, an aryl group, or a heterocyclic group. Aryl or alkyl sulfonyl moieties have the formula —$SO_2R'$, wherein R' is alkyl or aryl as defined herein, and include, but are not limited to, methylsulfonyl, ethylsulfonyl and phenylsulfonyl groups. A sulfonyl group can be unsubstituted or substituted. A phenylsulfonyl is optionally substituted with 1 to 3 substituents independently selected from halogen, alkyl, and alkoxy.

Unless otherwise indicated, when a substituent is deemed to be "optionally substituted," it is meant that the substituent is a group that may be substituted with one or more group(s) individually and independently selected from, for example, alkenyl, alkyl, alkoxy, alkylamine, alkylthio, alkynyl, amide, amino, including mono- and di-substituted amino groups, aryl, aryloxy, arylthio, carbonyl, carbocyclic, cyano, cycloalkyl, halogen, heteroalkyl, heteroalkenyl, heteroalkynyl, heteroaryl, heterocyclic, hydroxy, isocyanato, isothiocyanato, mercapto, nitro, O-carbamyl, N-carbamyl, O-thiocarbamyl, N-thiocarbamyl, C-amido, N-amido, S-sulfonamido, N-sulfonamido, C-carboxy, O-carboxy, perhaloalkyl, perfluoroalkyl, silyl, sulfonyl, thiocarbonyl, thiocyanato, trihalomethanesulfonyl, and the protected compounds thereof. The protecting groups that may form the protected compounds of the above substituents are known to those of skill in the art and may be found in references such as Greene and Wuts, Protective Groups in Organic Synthesis, 3$^{rd}$ Ed., John Wiley & Sons, New York, N.Y., 1999, and Kocienski, Protective Groups, Thieme Verlag, New York, N.Y., 1994, which are incorporated herein by reference in their entirety.

Certain Pharmaceutical Terminology

The term "acceptable" with respect to a formulation, composition or ingredient, as used herein, means having no persistent detrimental effect on the general health of the subject being treated.

The term "agonist", as used herein, refers to a molecule such as a compound, a drug, an enzyme activator or a hormone modulator which enhances the activity of another molecule or the activity of a receptor site.

The term "antagonist", as used herein, refers to a molecule such as a compound, a drug, an enzyme inhibitor, or a hormone modulator, which diminishes, or prevents the action of another molecule or the activity of a receptor site.

The term "carrier", as used herein, refers to relatively nontoxic chemical compounds or agents that facilitate the incorporation of a compound into cells or tissues.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount", as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case may be determined using techniques, such as a dose escalation study.

The terms "enhance" or "enhancing", as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "kit" and "article of manufacture" are used as synonyms.

The term "metabolite", as used herein, refers to a derivative of a compound which is formed when the compound is metabolized.

The term "active metabolite", as used herein, refers to a biologically active derivative of a compound that is formed when the compound is metabolized.

The term "metabolized", as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulfhydryl groups. Further information on metabolism may be obtained from *The Pharmacological Basis of Therapeutics*, 9th Edition, McGraw-Hill (1996).

The term "modulate", as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator", as used herein, refers to a molecule that interacts with a target either directly or indirectly. The interactions include, but are not limited to, the interactions of an agonist and an antagonist.

By "pharmaceutically acceptable", as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" of a compound, as used herein, refers to a salt that is pharmaceutically acceptable.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (1) and a co-agent, are both administered to a patient simultaneously in the form of a single entity or dosage. The term "non-fixed combination" means that the active ingredients, e.g. a compound of Formula (1) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition", as used herein, refers to a mixture of an active compound with other chemical components, such as carriers, stabilizers, diluents, dispersing agents, suspending agents, thickening agents, and/or excipients.

A "prodrug", as used herein, refers to a drug or compound in which metabolic processes within the body converts the drug or compound into a pharmacological active form.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment", as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition.

Illustrative Biological Activity

Mineralocorticoid Receptor (MR)

The mineralocorticoids are so named for their role in the metabolism of minerals, sodium, and potassium. The traditional role for these steroids has been in the regulation of fluid and electrolyte balance in epithelial tissues responsive to their effects, such as the kidney and the distal colon. Mineralocorticoid generating enzymes and receptors in nonepithelial tissues such as the heart and the vasculature, as well as the favorable effects of blockade of this pathway in diverse conditions such as heart failure and hypertension, have been identified.

In visceral tissues, such as the kidney and the gut, MR regulates sodium retention, potassium excretion, and water balance in response to aldosterone. Elevations in aldosterone levels, or excess stimulation of mineralocorticoid receptors, are linked to several pathological conditions or pathological disease states including, Conn's Syndrome, primary and secondary hyperaldosteronism, increased sodium retention, increased magnesium and potassium excretion (diuresis), increased water retention, hypertension (isolated systolic and combined systolic/diastolic), arrhythmias, myocardial fibrosis, myocardial infarction, Barter's Syndrome, congestive heart failure (CHF), and conditions associated with excess catecholamine levels. In addition, MR expression in the brain appears to play a role in the control of neuronal excitability, in the negative feedback regulation of the hypothalamic-pituitary-adrenal axis, and in the cognitive aspects of behavioral performance. In particular, mineralocorticoid receptors, and modulation of MR activity, are involved in anxiety and major depression. Finally, expression of MR may be related to differentiation of breast carcinomas. Compounds which selectively modulate MR would be of clinical importance in the treatment of or prevention of a variety of diseases and conditions, including, but not limited to, cancer, breast cancer, Conn's Syndrome, primary and secondary hyperaldosteronism, increased sodium retention, increased magnesium and potassium excretion (diuresis), increased water retention, hypertension (isolated systolic and combined systolic/diastolic), arrhythmias, myocardial fibrosis, myocardial infarction, Barter's Syndrome, congestive heart failure (CHF), conditions associated with excess catecholamine levels, cognitive dysfunctions, psychoses, cognitive conditions, memory disturbances, mood conditions, depression, bipolar condition, anxiety conditions, and personality conditions.

Glucocorticoid Receptor (GR).

Glucocorticoids, a class of corticosteroids, are endogenous hormones with profound effects on the immune system and multiple organ systems. They suppress a variety of immune and inflammatory functions by inhibition of inflammatory cytokines such as IL-1, IL-2, IL-6, and TNF, inhibition of arachidonic acid metabolites including prostaglandins and leukotrienes, depletion of T-lymphocytes, and reduction of the expression of adhesion molecules on endothelial cells. In addition to these effects, glucocorticoids stimulate glucose production in the liver and catabolism of proteins, play a role in electrolyte and water balance, reduce calcium absorption, and inhibit osteoblast function.

GR is expressed in almost all tissues and organ systems and is crucial for the integrity of the function of the central nervous system and the maintenance of cardiovascular, metabolic, and immune homeostasis. Glucocorticoids (e.g. cortisol, corticosterone, and cortisone), and the glucocorticoid receptor, have been implicated in the etiology of a variety of pathological conditions or pathologic disease states. For example, cortisol hypo-secretion is implicated in the pathogenesis of diseases resulting in muscle weakness, increased melanin pigmentation of the skin, weight loss, hypotension, and hypoglycemia. On the other hand, excessive or prolonged secretion of glucocorticoids has been correlated to Cushing's Syndrome and can also result in obesity, hypertension, glucose intolerance, hyperglycemia, diabetes mellitus, osteoporosis, polyuria, and polydipsia.

Compounds which selectively modulate GR would be of clinical importance in the treatment of or prevention of a variety of diseases and conditions, including, but not limited to, inflammation, tissue rejection, auto-immunity, malignancies such as leukemias and lymphomas, Cushing's syndrome, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, stroke and spinal cord injury, hypocalcemia, hyperglycemia, acute adrenal insufficiency, chronic primary adrenal insufficiency, secondary adrenal insufficiency, congenital adrenal hyperplasia, cerebral edema, thrombocytopenia, Little's syndrome, inflammatory bowel disease, systemic lupus erythematosus, polyartitis nodosa, Wegener's granulomatosis, giant cell arthritis, rheumatoid arthritis, osteoarthritis, hay fever, allergic rhinitis, urticaria, angioneurotic edema, chronic obstructive pulmonary disease, asthma, tendonitis, bursitis, Crohn's disease, ulcerative colitis, autoimmune chronic active hepatitis, organ transplantation, hepatitis, and cirrhosis; wound healing and tissue repair, inflammatory scalp alopecia, panniculitis, psoriasis, discoid lupus erythematosus, inflamed cysts, atopic dermatitis, pyoderma gangrenosum, pemphigus vulgaris, bullous pemphigoid, systemic lupus erythematosus, dermatomyositis, eosinophilic fasciitis, relapsing polychondritis, inflammatory vasculitis, sarcoidosis, Sweet's disease, type I reactive leprosy, capillary hemangiomas, contact dermatitis, atopic dermatitis, lichen planus, exfoliative dermatitis, erythema no do sum, acne, hirsutism, toxic epidermal necrolysis, erythema multiform, cutaneous T-cell lymphoma, emphysema, neuroinflammatory conditions, multiple sclerosis and Alzheimer's disease.

Androgen Receptor (AR)

Androgens bind to a specific receptor, the androgen receptor (AR), inside the cells of target tissues. The AR is expressed in numerous tissues of the body and is the receptor through which the physiological as well as the pathophysiological effects of endogenous androgen ligands, such as testosterone (T) and dihydrotestosterone (DHT), are expressed. Structurally, the AR is composed of three main functional domains: the ligand binding domain (LBD), the DNA-binding domain, and amino-terminal domain. A compound that binds to the AR and mimics the effects of an endogenous AR ligand is referred to as an AR agonist, whereas a compound that inhibits the effects of an endogenous AR ligand is termed an AR antagonist. Binding of androgen to the receptor activates it and causes it to bind to DNA binding sites adjacent to target genes. From there it interacts with coactivator proteins and basic transcription factors to regulate the expression of the gene. Thus, via its receptor, androgens cause changes in gene expression in cells. These changes ultimately have consequences on the metabolic output, differentiation or proliferation of the cell that are visible in the physiology of the target tissue.

Compounds which selectively modulate AR would be of clinical importance in the treatment of or prevention of a variety of diseases and conditions, including, but not limited to, prostate cancer, benign prostatic hyperplasia, hirsutism in women, alopecia, anorexia nervosa, breast cancer, acne, musculoskeletal conditions, such as bone disease, hematopoietic conditions, neuromuscular disease, rheumatological disease, wasting disease, cancer, AIDS, cachexia, for hormone replacement therapy (HRT), employed in male contraception, for male performance enhancement, for male reproductive conditions, and primary or secondary male hypogonadism.

Estrogen Receptor (ER)

Estrogens play important roles in the development and homeostasis of the reproductive, central nervous, skeletal, and cardiovascular systems of both males and females. The estrogen receptor (ER) is expressed in a number of tissues including prostate, bladder, ovary, testis, lung, small intestine, vascular endothelium, and various parts of the brain. Compounds which selectively modulate ER would be of clinical importance in the treatment of or prevention of a variety of diseases and conditions, including, but not limited to, prostate cancer, testicular cancer, ovarian cancer, lung cancer, cardiovascular diseases, neurodegenerative conditions, urinary incontinence, CNS conditions, multiple sclerosis, GI tract conditions, osteoporosis, bone loss, bone fractures, osteoporosis, Paget's disease, abnormally increased bone turnover, periodontal disease, tooth loss, rheumatoid arthritis, osteoarthritis, periprosthetic osteolysis, osteogenesis imperfecta, metastatic bone disease, hypercalcemia of malignancy, and multiple myeloma, cartilage degeneration, endometriosis, uterine fibroid disease, breast cancer, uterine cancer, hot flashes, impairment of cognitive function, cerebral degenerative conditions, restenosis, gynecomastia, vascular smooth muscle cell proliferation, obesity and incontinence.

Progesterone Receptor (PR).

Progesterone is a steroid hormone known primarily for its role in development and maintenance of the reproductive system. Progesterone is the natural ligand for the PR and when bound a receptor/ligand complex is formed. This complex binds to specific gene promoters present in the cell's DNA and modulates the production of mRNA and protein encoded by that gene. Synthetic ligands for PR can be agonists, which mimic the action of the natural hormone, or they can be antagonists, which inhibits the effect of the hormone.

Progesterone has been implicated in a wide range of biological processes outside of the reproductive tract. In the peripheral nervous system progesterone promotes myelination of regenerating nerves. Progesterone is synthesized by Schwann cells (the cell type which produces myelin), and PR has been detected in primary Schwann cell cultures from rats, suggesting the presence of an autocrine loop. Progesterone appears to promote myelin formation by binding to PR and stimulating transcription of the transcription factor Krox-20, which in turn stimulates transcription of several myelin protein genes. Thus, both local and systemic production of progesterone may contribute to neurofibroma growth. Therefore, compounds which selectively modulate PR would be of clinical importance in the treatment of or prevention of a variety of diseases and conditions, including, but not limited to, hormone dependent breast cancers, uterine and ovarian cancers, non-malignant chronic diseases and conditions such as fibroids, hormone dependent prostate cancer, and in hormone replacement therapy.

Compounds

Compounds of Formula (A), pharmaceutically acceptable salts, pharmaceutically acceptable N-oxides, pharmaceutically active metabolites, pharmaceutically acceptable prodrugs, and pharmaceutically acceptable solvates thereof, modulate the activity of steroid hormone nuclear receptors and, as such, are useful for treating diseases or conditions in which aberrant steroid hormone nuclear receptor activity contributes to the pathology and/or symptoms of a disease or condition.

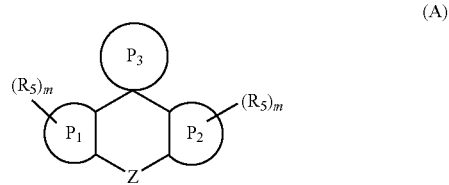

(A)

In compounds of Formula (A), the ring structures of $P_1$ and $P_2$ are independently selected from optionally substituted cycloalkyl, heterocycloalkyl, aryl, and heteroaryl. In addition, the ring structures of $P_1$ and $P_2$ are independently comprised of 5 to 8 atoms. When the ring structures of $P_1$ and $P_2$ are substituted then each $R_5$ is independently selected from halogen, OH, $NH_2$, SH, $NO_2$, CN, and an optionally substituted moiety selected from $-L_2$-alkyl, $-L_2$-cycloalkyl, $-L_2$-heteroalkyl, $-L_2$-haloalkyl, $-L_2$-aryl, $-L_2$-heterocycloalkyl, and -L$_2$-heteroaryl, wherein L$_2$ is selected from a bond, O, NH, S, —C(O)—, —C(S)—, —C(O)O—, —C(O)NH—, —S(O)—, —S(O)$_2$, and —S(O)NH—, and each m is independently selected from 0, 1, 2, 3, 4, 5, and 6. The group designated as Z is CR$_6$=CR$_6$ or C(R$_6$)$_2$—C(R$_6$)$_2$, with each R$_6$ independently selected from H, halogen, OH, NH$_2$, SH, NO$_2$, CN, and an optionally substituted moiety selected from -L$_2$-alkyl, -L$_2$-cycloalkyl, -L$_2$-heteroalkyl, -L$_2$-haloalkyl, -L$_2$-aryl, -L$_2$-heterocycloalkyl, and -L$_2$-heteroaryl, wherein L$_2$ is selected from a bond, O, NH, S, —C(O)—, —C(S)—, —C(O)O—, —C(O)NH—, —S(O)—, —S(O)$_2$, and —S(O)NH—, or any two R$_6$ groups can together form a 3 to 8-membered cycloalkyl, heterocycloalkyl, aryl, or heteroaryl ring.

In addition, the ring structure P$_3$ of compounds of Formula (A) is a spiro structure comprised of 5, 6, 7, or 8 atoms, and structure X, wherein X is selected from O, NR$_7$, C(R$_8$)$_2$, and S. Alternatively, the ring structure P$_3$ is a spiro structure comprised of 5, 6, 7, or 8 atoms, and structures X and A, wherein X is selected from O, NR$_7$, C(R$_8$)$_2$, and S, while A is NR$_1$—CR$_2$R$_3$ or N=CR$_2$; wherein R$_1$ is H, or an optionally substituted moiety selected from -L$_1$-alkyl, -L$_1$-cycloalkyl, -L$_1$-heteroalkyl, -L$_1$-haloalkyl, -L$_1$-aryl, -L$_1$-heterocycloalkyl, and -L$_1$-heteroaryl, wherein L$_1$ is selected from a bond, —C(O)—, —C(S)—, —C(O)O—, —C(O)NH—, —S(O)—, —S(O)$_2$, and —S(O)NH—. The substituents R$_2$ and R$_3$ are independently selected from H, halogen, OH, NH$_2$, SH, NO$_2$, CN, and an optionally substituted moiety selected from -L$_2$-alkyl, -L$_2$-cycloalkyl, -L$_2$-heteroalkyl, -L$_2$-haloalkyl, -L$_2$-aryl, -L$_2$-heterocycloalkyl, and L$_2$-heteroaryl, wherein L$_2$ is selected from a bond, O, NH, S, —C(O)—, —C(S)—, —C(O)O—, —C(O)NH—, —S(O)—, —S(O)$_2$, and —S(O)NH—; or the substituents R$_1$ and R$_2$ together form an optionally substituted 3 to 8-membered heterocyclic ring; or the substituents R$_2$ and R$_3$ together form an optionally substituted 3 to 8-membered carbocyclic or heterocyclic ring. Each R$_7$ and R$_8$ are independently selected from H and (C$_1$-C$_4$)alkyl. The ring structure P$_3$ may be further substituted with two R$_4$ groups, wherein each R$_4$ is independently selected from H, halogen, OH, NH$_2$, SH, NO$_2$, CN, and an optionally substituted moiety selected from -L$_2$-alkyl, -L$_2$-cycloalkyl, -L$_2$-heteroalkyl, -L$_2$-haloalkyl, -L$_2$-aryl, -L$_2$-heterocycloalkyl, and -L$_2$-heteroaryl, wherein L$_2$ is selected from a bond, O, NH, S, —C(O)—, —C(S)—, —C(O)O—, —C(O)NH—, —S(O)—, —S(O)$_2$, and —S(O)NH—, as long as at least one R$_4$ is not H.

Additional embodiments of Formula (A) are shown below as Formula (B), Formula (C), Formula (E), Formula (F), Formula (G), Formula (H), Formula (I), Formula (J), Formula (K), Formula (1), Formula (2), Formula (4), Formula (5), and Formula (6).

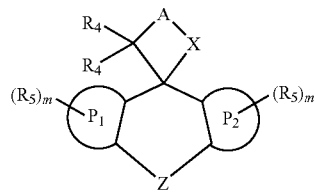

(B)

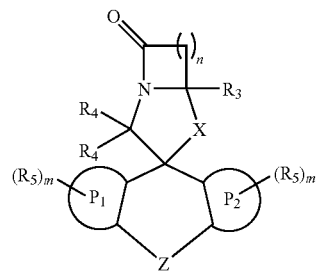

(C)

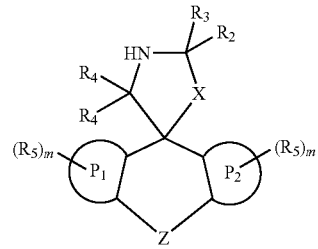

(E)

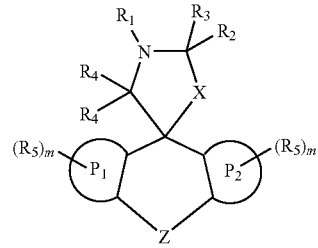

(F)

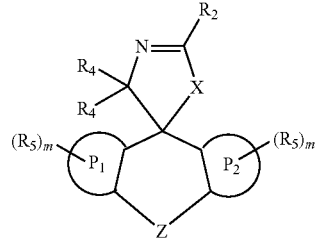

(G)

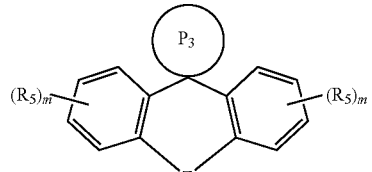

(H)

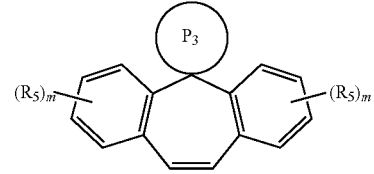

(I)

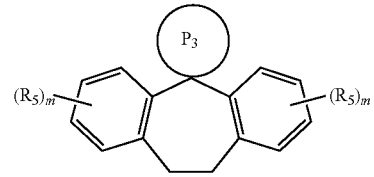

(J)

-continued

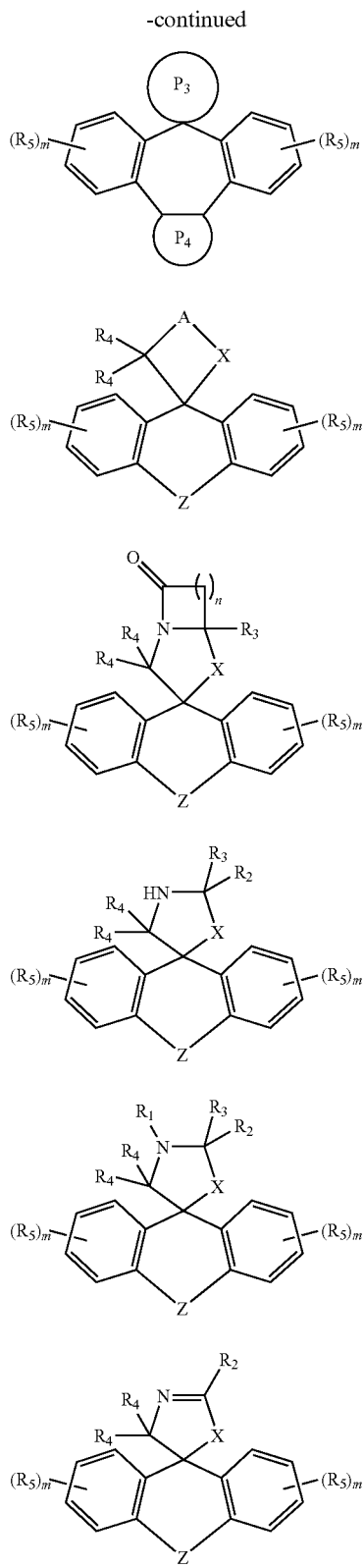

(K)

(1)

(2)

(4)

(5)

(6)

In addition, compounds having the structure of Formula (D) or Formula (3), while not falling within the scope of Formula (A), are compositions described herein and find use in the methods described herein:

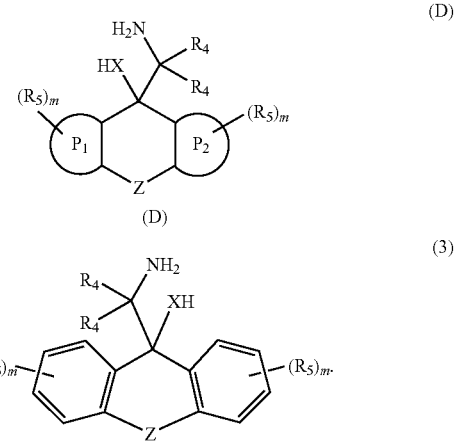

(D)

(D)

(3)

Synthesis of the Compounds

Compounds of Formula (1) and compounds having the structures described in the prior section may be synthesized using standard synthetic techniques known to those of skill in the art or using methods known in the art in combination with methods described herein. In additions, solvents, temperatures and other reaction conditions presented herein may vary according to those of skill in the art.

The starting material used for the synthesis of the compounds of Formula (1) and compounds having the structures described in the prior section as described herein can be obtained from commercial sources, such as Aldrich Chemical Co. (Milwaukee, Wis.), Sigma Chemical Co. (St. Louis, Mo.), or the starting materials can be synthesized. The compounds described herein, and other related compounds having different substituents can be synthesized using techniques and materials known to those of skill in the art, such as described, for example, in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001), and Green and Wuts, PROTECTIVE GROUPS IN ORGANIC SYNTHESIS 3$^{rd}$ Ed., (Wiley 1999) (all of which are incorporated by reference in their entirety). General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein. As a guide the following synthetic methods may be utilized.

Formation of Covalent Linkages by Reaction of an Electrophile with a Nucleophile The compounds described herein can be modified using various electrophiles or nucleophiles to form new functional groups or substituents. Table 1 entitled "Examples of Covalent Linkages and Precursors Thereof" lists selected examples of covalent linkages and precursor functional groups which yield and can be used as guidance toward the variety of electrophiles and nucleophiles combinations available. Precursor functional groups are shown as electrophilic groups and nucleophilic groups.

TABLE 1

Examples of Covalent Linkages and Precursors Thereof

| Covalent Linkage Product | Electrophile | Nucleophile |
|---|---|---|
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Hydrazones | aldehydes or ketones | Hydrazines |
| Oximes | aldehydes or ketones | Hydroxylamines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | alkyl sulfonates | carboxylic acids |
| Ethers | alkyl sulfonates | alcohols/phenols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Boronate esters | Boronates | Glycols |
| Carboxamides | carboxylic acids | amines/anilines |
| Esters | carboxylic acids | Alcohols |
| hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ammotriazines | halotriazines | amines/anilines |
| Triazinyl ethers | halotriazines | alcohols/phenols |
| Amidines | imido esters | amines/anilines |
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Phosphite esters | phosphoramidites | Alcohols |
| Silyl ethers | silyl halides | Alcohols |
| Alkyl amines | sulfonate esters | amines/anilines |
| Thioethers | sulfonate esters | Thiols |
| Esters | sulfonate esters | carboxylic acids |
| Ethers | sulfonate esters | Alcohols |
| Sulfonamides | sulfonyl halides | amines/anilines |
| Sulfonate esters | sulfonyl halides | phenols/alcohols |

Use of Protecting Groups

In the reactions described, it may be necessary to protect reactive functional groups, for example hydroxy, amino, imino, thio or carboxy groups, where these are desired in the final product, to avoid their unwanted participation in the reactions. Protecting groups are used to block some or all reactive moieties and prevent such groups from participating in chemical reactions until the protective group is removed. It is preferred that each protective group be removable by a different means. Protective groups that are cleaved under totally disparate reaction conditions fulfill the requirement of differential removal. Protective groups can be removed by acid, base, and hydrogenolysis. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, or they may be blocked with oxidatively-removable protective groups such as 2,4-dimethoxybenzyl, while co-existing amino groups may be blocked with fluoride labile silyl carbamates.

Allyl blocking groups are useful in then presence of acid- and base-protecting groups since the former are stable and can be subsequently removed by metal or pi-acid catalysts. For example, an allyl-blocked carboxylic acid can be deprotected with a $Pd_0$-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

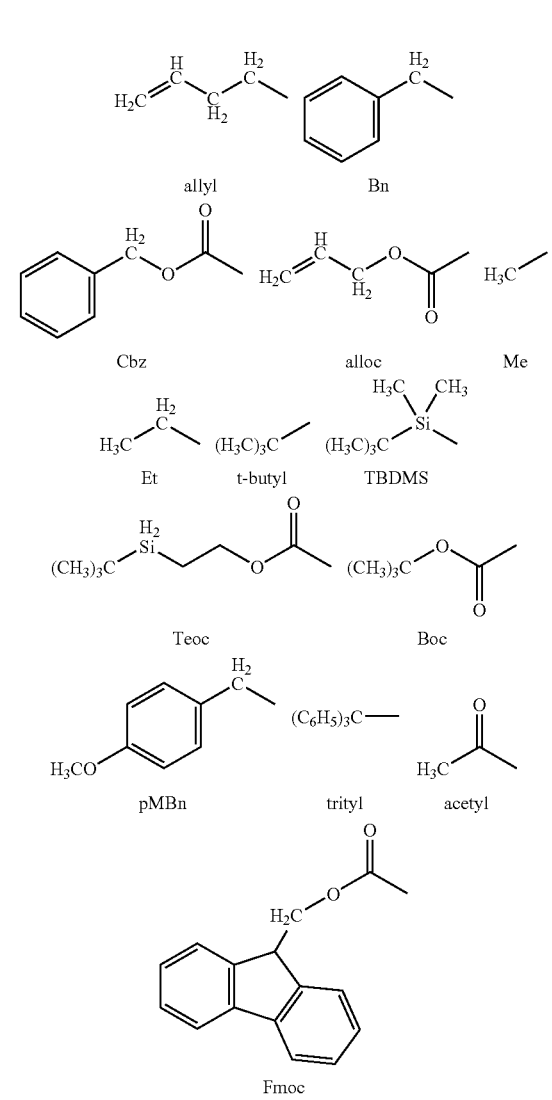

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference in their entirety.

Compounds of Formula (A) can be synthesized according to reaction Scheme 1, wherein the initial tri-cyclic starting material comprises a reactive center (G) used to form di-nucleophilie compounds, which are further reacted with various electrophilic reagents to create spiro-containing compounds.

Scheme 1

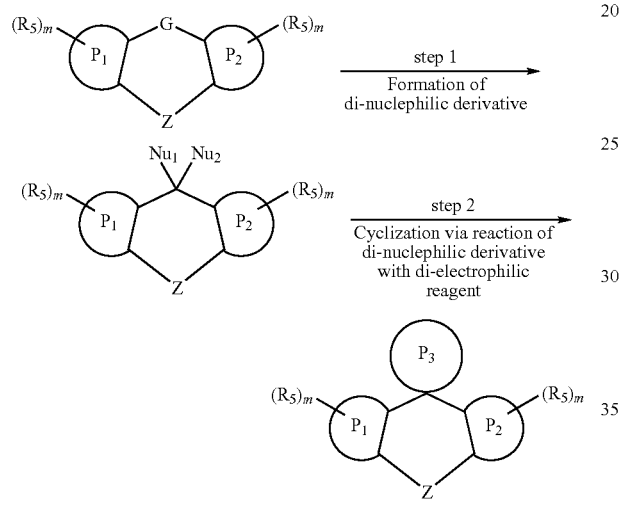

A non-limiting example of step 1 for the synthetic route toward a di-nucleophilic compound is given in reaction Scheme 2, wherein a tri-cyclic compound with a ketone moiety is treated with trimethylsilyl cyanide (TMSCN) to afford the trimethylsiloxy- and cyano-substituted compound, which is then reduced using lithium aluminum hydride, or any other suitable reducing agent, to yield the di-nucleophilic hydroxyamine compound (D), when X=O.

Scheme 2

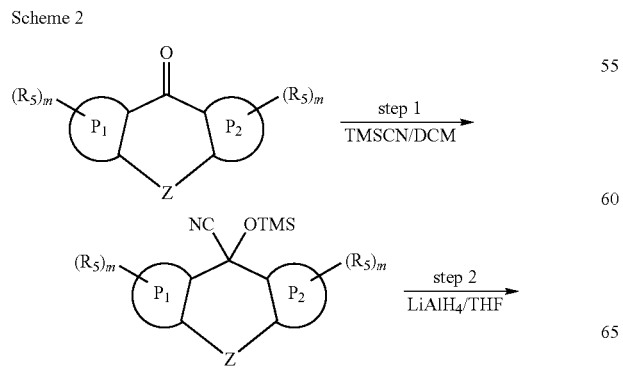

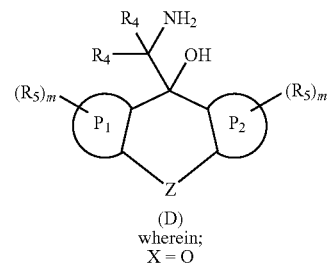

(D)
wherein;
X = O

In particular, the synthesis of di-nucleophilic suberenone compounds (3a) is shown, by way of example only, in reaction Scheme 3. In this example the tri-cyclic starting material is an optionally substituted dibenzosuberenone compound.

Scheme 3

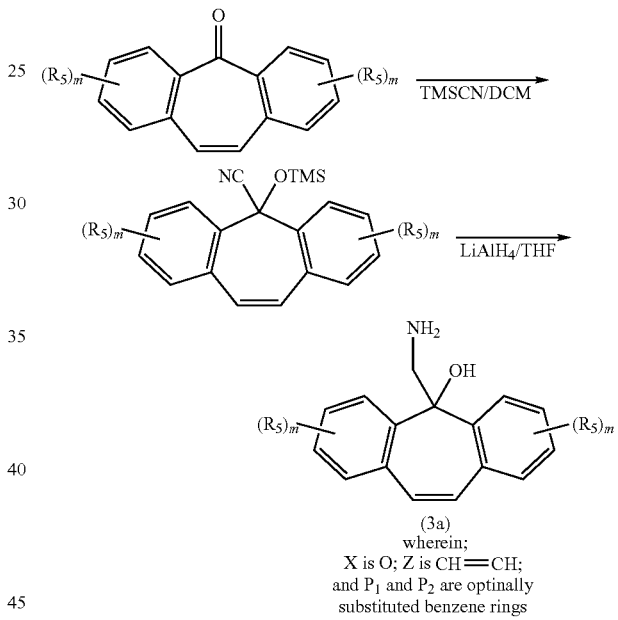

(3a)
wherein;
X is O; Z is CH=CH;
and $P_1$ and $P_2$ are optinally substituted benzene rings Alternatively, the synthesis of di-nucleophilic suberone compounds (3b) is shown, by way of example only, in reaction Scheme 4. In this example the tri-cyclic starting material is an optionally substituted dibenzosuberone compound.

Scheme 4

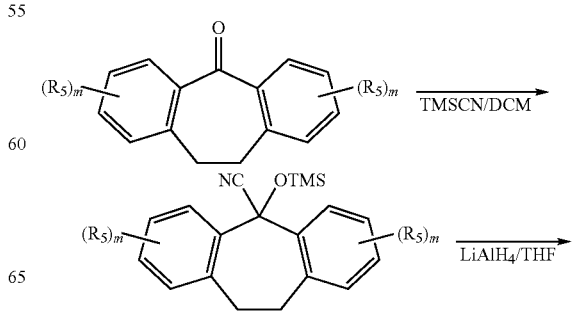

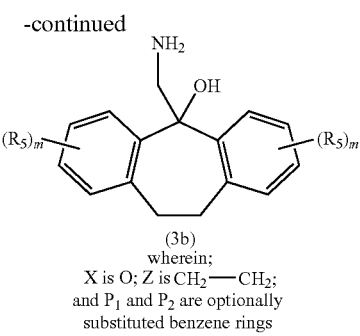

(3b)
wherein;
X is O; Z is CH$_2$—CH$_2$;
and P$_1$ and P$_2$ are optionally
substituted benzene rings In addition, compounds of Formula (D) in which X is S may be synthesized, by way of example only, according to reaction Scheme 5. Starting material such as, by way of example only, optionally substituted dibenzosuberenone or optionally substituted dibenzosuberone, react with a suitable reagent, such as, by way of example only, Lawesson's reagent, to form the thioketone compound, which is treated with a suitable cyano nucleophilic reagent, such as, by way of example only, HCN, to form the cyano/thiol compound. Reduction of the cyano/thiol compound with a suitable reducing reagent, such as, by way of example only, lithium aluminum hydride, affords the thio-amino-dinucleophilic compound.

Scheme 5

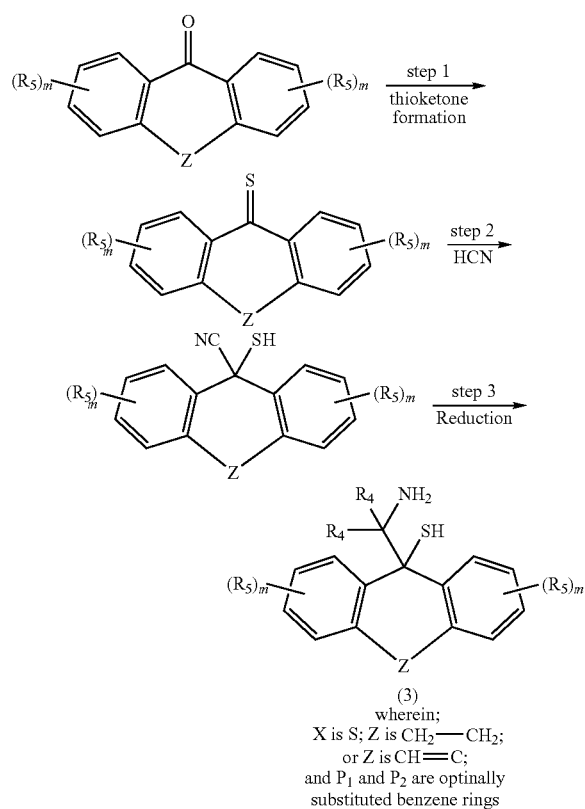

(3)
wherein;
X is S; Z is CH$_2$—CH$_2$;
or Z is CH═C;
and P$_1$ and P$_2$ are optionally
substituted benzene rings In addition, compounds of Formula (D) in which X is N may be synthesized, according to the exemplary reaction Scheme 6. Starting material such as, by way of example only, optionally substituted dibenzosuberenone or optionally substituted dibenzosuberone, react with a suitable reagent, such as, by way of example only, hydroxylamine, to form the oxime compound. The oxime compound reacts with a suitable cyano nucleophilic reagent, such as, by way of example only, HCN, and then is treated with a suitable reducing reagent, such as, by way of example only, lithium aluminum hydride, to afford the di-amino compound.

Scheme 6

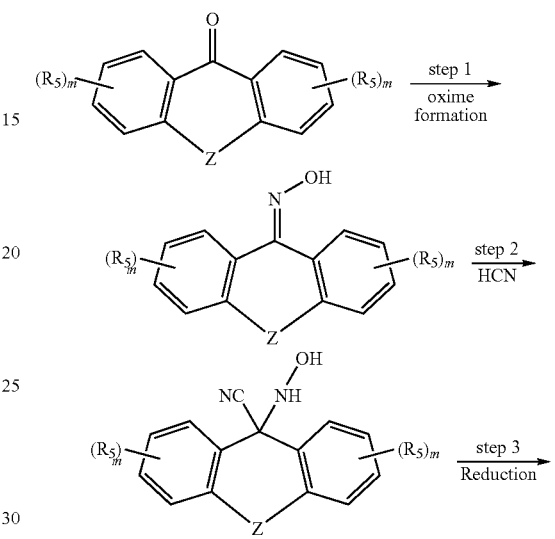

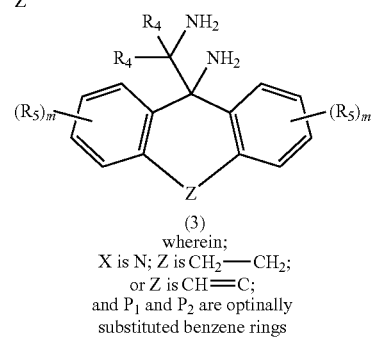

(3)
wherein;
X is N; Z is CH$_2$—CH$_2$;
or Z is CH═C;
and P$_1$ and P$_2$ are optinally
substituted benzene rings The intermediate compounds of Formula (D), including, but not limited to, compound (3a) and compound (3b), may be used to synthesize compounds of Formula (A) and structurally similar compounds disclosed herein. For example, a non-limiting synthetic scheme for the formation of fused-ring spiro-compounds of Formula (C) is shown in reaction Scheme 7, wherein the di-nucleophilic compound (D) reacts with a keto-acid to generated the fused-ring spiro-compound (2) via a cyclocondensation reaction.

Scheme 7

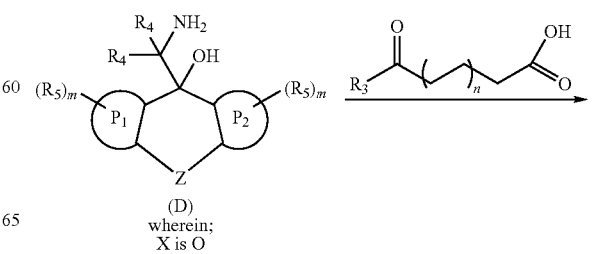

(D)
wherein;
X is O

-continued

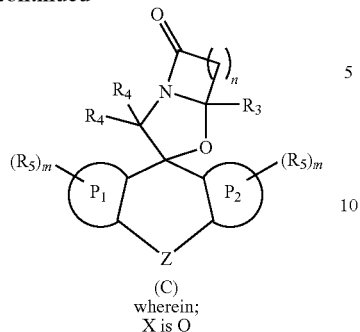

(C)
wherein;
X is O

Synthesis of fused-ring spiro-compounds of Formula (A) is further exemplified in reaction Scheme 8, wherein the optionally substituted suberenone (3a) or the optionally substituted suberone (3b) are reacted with a keto-acid to afford the fused-ring spiro-compound (2).

Scheme 8

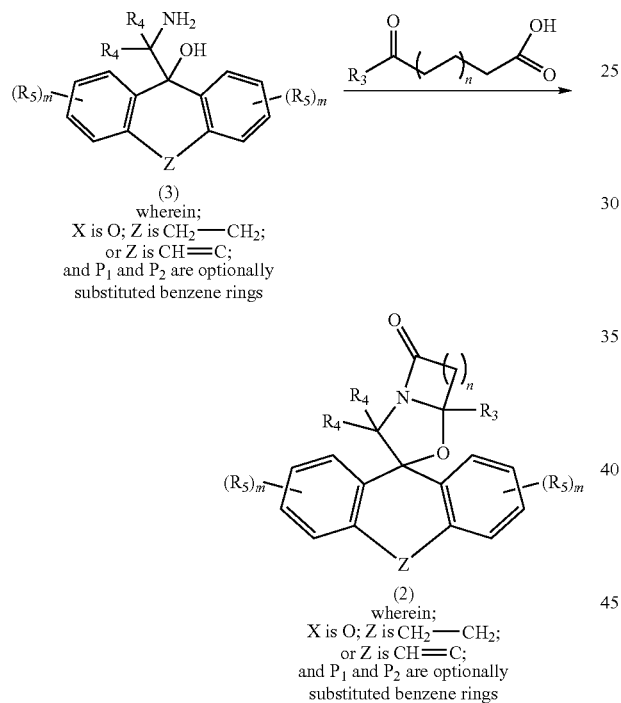

Exemplary synthesis of oxazoline Spiro compounds of Formula (A) is shown in Scheme 9, wherein the di-nucleophilic compound (D) reacts with an imidate compound to afford the oxazoline Spiro compound (G). Note that R' is not incorporated into the final product.

Scheme 9

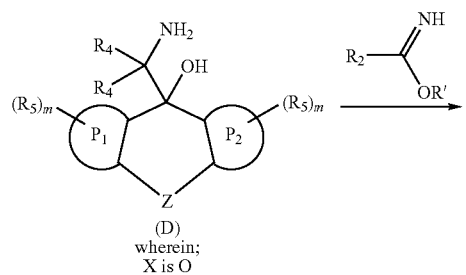

(D)
wherein;
X is O

-continued

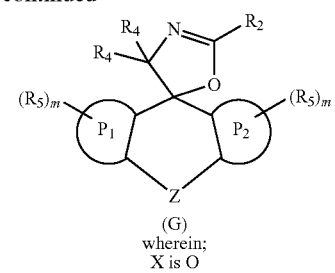

(G)
wherein;
X is O

Synthesis of oxazoline spiro compounds of Formula (A) is further exemplified in reaction Scheme 10, wherein the optionally substituted suberenone (3a) or the optionally substituted suberone (3b) are reacted with an imidate to afford the oxazoline spiro compounds (6).

Scheme 10

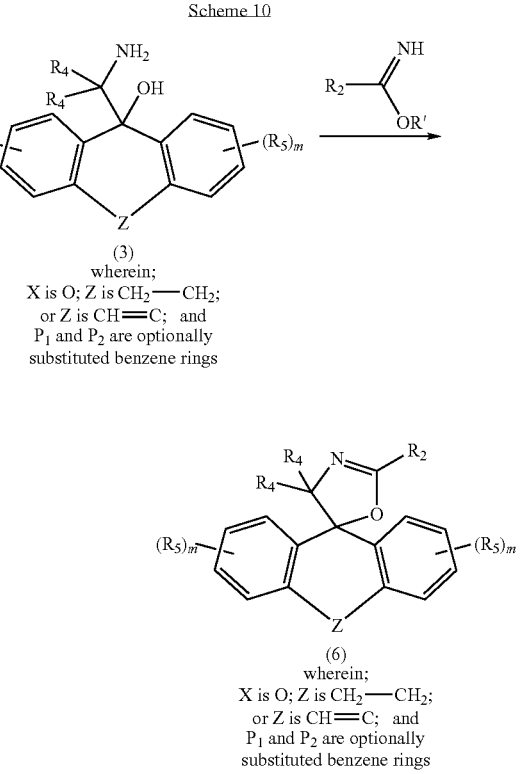

Exemplary synthesis of oxazolidine spiro compounds of Formula (A) is shown in scheme 11, wherein the di-nucleophilic compound (D) reacts with a ketone compound to afford the oxazolidine spiro compound (E). Substituted oxazolidine spiro compounds of Formula (A) may be synthesized by reaction of oxazolidine spiro compounds (E) with acid chlorides, anhydrides, isocyanates, isothiocyanates, or sulfonyl chlorides, or the like, to give the substituted oxazolidine spiro compounds (F), also shown in reaction Scheme 11 as a non-limiting example.

Scheme 11

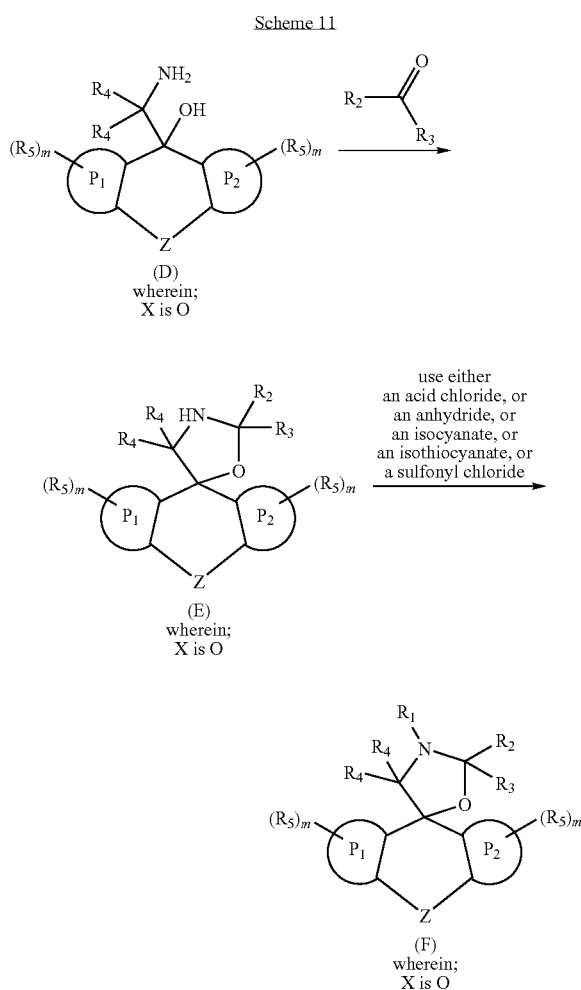

(D) wherein; X is O (E) wherein; X is O (F) wherein; X is O

Synthesis of oxazolidine Spiro compounds of Formula (A) is further exemplified in reaction Scheme 12, wherein the optionally substituted suberenone (3a) or the optionally substituted suberone (3b) are reacted with a ketone to afford the oxazolidine spiro compounds (4), which can be further reacted with acid chlorides, anhydrides, isocyanates, isothiocyanates, or sulfonyl chlorides, or the like, to give the substituted oxazolidine spiro compounds (5).

Scheme 12

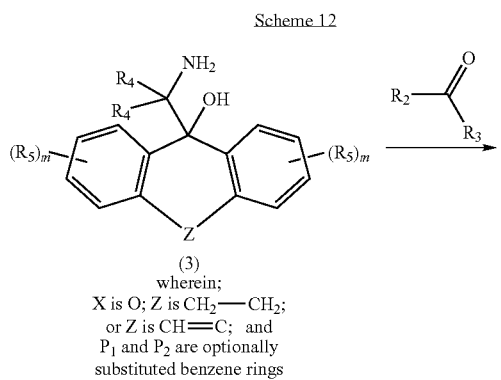

(3)
wherein;
X is O; Z is CH$_2$—CH$_2$;
or Z is CH═C; and
P$_1$ and P$_2$ are optionally
substituted benzene rings

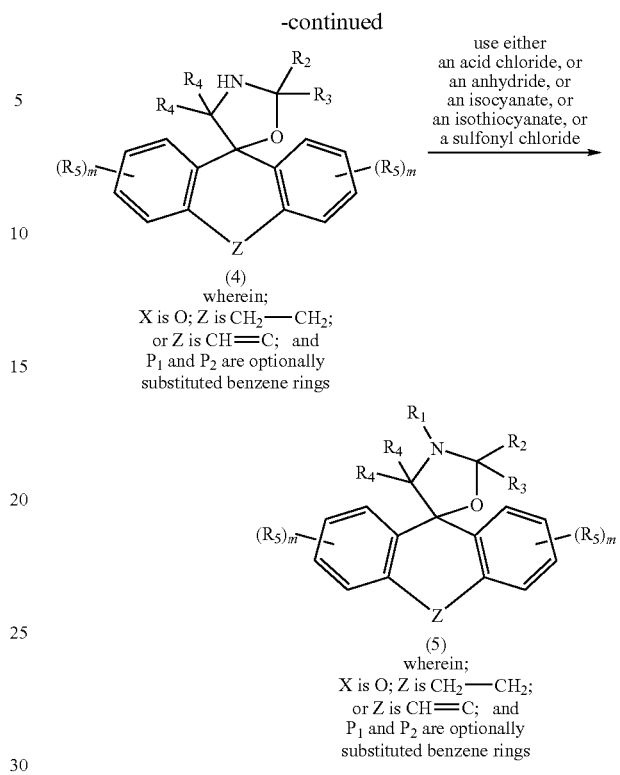

(4)
wherein;
X is O; Z is CH$_2$—CH$_2$;
or Z is CH═C; and
P$_1$ and P$_2$ are optionally
substituted benzene rings (5)
wherein;
X is O; Z is CH$_2$—CH$_2$;
or Z is CH═C; and
P$_1$ and P$_2$ are optionally
substituted benzene rings

Further Forms of Compounds

For convenience, the form and other characteristics of the compounds described in this section and other parts herein use a single formula, such as "Formula (1)," by way of example. However, the form and other characteristics of the compounds described herein apply equally well to all formulas presented herein that fall within the scope of Formula (A). For example, the form and other characteristics of the compounds described herein can be applied to compounds having the structure of Formula (B), Formula (C), Formula (E), Formula (F), Formula (G), Formula (H), Formula (I), Formula (J), Formula (K), Formula (1), Formula (2), Formula (4), Formula (5), Formula (6), as well as to all of the specific compounds that fall within the scope of these generic formula.

Compounds of Formula (1) can be prepared as a pharmaceutically acceptable salts formed when an acidic proton present in the parent compound either is replaced by a metal ion, for example an alkali metal ion, an alkaline earth ion, or an aluminum ion; or coordinates with an organic base. In addition, the salt forms of the disclosed compounds can be prepared using salts of the starting materials or intermediates.

Compounds of Formula (1) can be prepared as a pharmaceutically acceptable acid addition salt (which is a type of a pharmaceutically acceptable salt) by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, Q-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

Alternatively, compounds of Formula (1) can be prepared as a pharmaceutically acceptable base addition salts (which is a type of a pharmaceutically acceptable salt) by reacting the free acid form of the compound with a pharmaceutically acceptable inorganic or organic base, including, but not limited to organic bases such as ethanolamine, diethanolamine, triethanolamine, tromethamine, N-methylglucamine, and the like and inorganic bases such as aluminum hydroxide, calcium hydroxide, potassium hydroxide, sodium carbonate, sodium hydroxide, and the like.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol; and the like. Hydrates are formed when the solvent is water, or alcoholates are formed when the solvent is alcohol. Solvates of compounds of Formula (1) can be conveniently prepared or formed during the processes described herein. By way of example only, hydrates of compounds of Formula (1) can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Compounds of Formula (1) include crystalline forms, also known as polymorphs. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

Compounds of Formula (1) in unoxidized form can be prepared from N-oxides of compounds of Formula (1) by treating with a reducing agent, such as, but not limited to, sulfur, sulfur dioxide, triphenyl phosphine, lithium borohydride, sodium borohydride, phosphorus trichloride, tribromide, or the like in a suitable inert organic solvent, such as, but not limited to, acetonitrile, ethanol, aqueous dioxane, or the like at 0 to 80° C.

Compounds of Formula (1) can be prepared as prodrugs. Prodrugs are generally drug precursors that, following administration to a subject and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound of Formula (1) which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

Prodrugs may be designed as reversible drug derivatives, for use as modifiers to enhance drug transport to site-specific tissues. The design of prodrugs to date has been to increase the effective water solubility of the therapeutic compound for targeting to regions where water is the principal solvent. See, e.g., Fedorak et al., *Am. J. Physiol.,* 269:G210-218 (1995); McLoed et al., *Gastroenterol,* 106:405-413 (1994); Hochhaus et al., *Biomed. Chrom.,* 6:283-286 (1992); J. Larsen and H. Bundgaard, *Int. J. Pharmaceutics,* 37, 87 (1987); J. Larsen et al., *Int. J. Pharmaceutics,* 47, 103 (1988); Sinkula et al., *J. Pharm. Sci.,* 64:181-210 (1975); T. Higuchi and V. Stella, *Pro-drugs as Novel Delivery Systems,* Vol. 14 of the A.C.S. Symposium Series; and Edward B. Roche, *Bioreversible Carriers in Drug Design,* American Pharmaceutical Association and Pergamon Press, 1987, all incorporated herein in their entirety.

Additionally, prodrug derivatives of compounds of Formula (1) can be prepared by methods known to those of ordinary skill in the art (e.g., for further details see Saulnier et al., (1994), Bioorganic and Medicinal Chemistry Letters, Vol. 4, p. 1985). By way of example only, appropriate prodrugs can be prepared by reacting a non-derivatized compound of Formula (1) with a suitable carbamylating agent, such as, but not limited to, 1,1-acyloxyalkylcarbanochloridate, para-nitrophenyl carbonate, or the like. Prodrug forms of the herein described compounds, wherein the prodrug is metabolized in vivo to produce a derivative as set forth herein are included within the scope of the claims. Indeed, some of the herein-described compounds may be a prodrug for another derivative or active compound.

Sites on the aromatic ring portion of compounds of Formula (1) can be susceptible to various metabolic reactions, therefore incorporation of appropriate substituents on the aromatic ring structures, such as, by way of example only, halogens can reduce, minimize or eliminate this metabolic pathway.

The compounds described herein may be labeled isotopically (e.g. with a radioisotope) or by another other means, including, but not limited to, the use of chromophores or fluorescent moieties, bioluminescent labels, or chemiluminescent labels. The compounds of Formula (1) may possess one or more chiral centers and each center may exist in the R or S configuration. The compounds presented herein include all diastereomeric, enantiomeric, and epimeric forms as well as the appropriate mixtures thereof. Compounds of Formula (1) can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds described herein, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities.

The diastereomers can be separated by chiral chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981, herein incorporated by reference in its entirety.

Additionally, the compounds and methods provided herein may exist as geometric isomers. The compounds and methods provided herein include all cis, trans, syn, anti, entgegen (E), and zusammen (Z) isomers as well as the appropriate mixtures thereof. In some situations, compounds may exist as tautomers. All tautomers are included within the formulas described herein are provided by compounds and methods herein. In additional embodiments of the compounds and methods provided herein, mixtures of enantiomers and/or diastereoisomers, resulting from a single preparative step, combination, or interconversion may also be useful for the applications described herein.

Pharmaceutical Composition/Formulation/Administration

For convenience, the pharmaceutical compositions and formulations described in this section and other parts herein use a single formula, such as "Formula (1)," by way of example. However, the pharmaceutical compositions and formulations described herein apply equally well to all formulas presented herein that fall within the scope of Formula (A). For example, the pharmaceutical compositions and formulations described herein can be applied to compounds having the structure of Formula (B), Formula (C), Formula (E), Formula (F), Formula (G), Formula (H), Formula (I), Formula (J), Formula (K), Formula (1), Formula (2), Formula (4), Formula (5), Formula (6), as well as to all of the specific compounds that fall within the scope of these generic formula.

A pharmaceutical composition, as used herein, refers to a mixture of a compound of Formula (1) with other chemical components, such as carriers, stabilizers, diluents, dispersing agents, suspending agents, thickening agents, and/or excipients. The pharmaceutical composition facilitates administration of the compound to an organism. Pharmaceutical composition containing compounds of Formula (1) can be administered in therapeutically effective amounts as pharmaceutical compositions by any conventional form and route known in the art including, but not limited to: intravenous, oral, rectal, aerosol, parenteral, ophthalmic, pulmonary, transdermal, vaginal, otic, nasal, and topical administration.

One may administer the compound in a local rather than systemic manner, for example, via injection of the compound directly into an organ, often in a depot or sustained release formulation. Furthermore, one may administer pharmaceutical composition containing compounds of Formula (1) in a targeted drug delivery system, for example, in a liposome coated with organ-specific antibody. The liposomes will be targeted to and taken up selectively by the organ. In addition, the pharmaceutical composition containing compounds of Formula (1) may be provided in the form of a rapid release formulation, in the form of an extended release formulation, or in the form of an intermediate release formulation.

For oral administration, compounds of Formula (1) can be formulated readily by combining the active compounds with pharmaceutically acceptable carriers or excipients well known in the art. Such carriers enable the compounds described herein to be formulated as tablets, powders, pills, dragees, capsules, liquids, gels, syrups, elixirs, slurries, suspensions and the like, for oral ingestion by a patient to be treated.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal or sublingual administration, the compositions may take the form of tablets, lozenges, or gels formulated in conventional manner. Parental injections may involve for bolus injection or continuous infusion. The pharmaceutical composition of Formula (1) may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds of Formula (1) can be administered topically and can be formulated into a variety of topically administrable compositions, such as solutions, suspensions, lotions, gels, pastes, medicated sticks, balms, creams or ointments.

Such pharmaceutical compounds can contain solubilizers, stabilizers, tonicity enhancing agents, buffers and preservatives.

Formulations suitable for transdermal administration of compounds having the structure of Formula (1) may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the compounds of Formula (1) can be accomplished by means of iontophoretic patches and the like. Additionally, transdermal patches can provide controlled delivery of the compounds Formula (1). The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

For administration by inhalation, the compounds of Formula (1) maybe in a form as an aerosol, a mist or a powder. Pharmaceutical compositions of Formula (1) are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, such as, by way of example only, gelatin for use in an inhaler or insufflator may be formulated containing a powder mix of the compound and a suitable powder base such as lactose or starch.

The compounds of Formula (1) may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In practicing the methods of treatment or use provided herein, therapeutically effective amounts of compounds of Formula (1) provided herein are administered in a pharmaceutical composition to a mammal having a disease or condition to be treated. Preferably, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

Pharmaceutical compositions may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. Pharmaceutical compositions comprising a compound of Formula (1) may be manufactured in a conventional manner, such as, by way of example only, by means of conventional mixing, dissolving, granulating, dragee-making, levigating, emulsifying, encapsulating, entrapping or compression processes.

The pharmaceutical compositions will include at least one pharmaceutically acceptable carrier, diluent or excipient and a compound of Formula (1) described herein as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. In some situations, compounds may exist as tautomers. All tautomers are included within the scope of the compounds presented herein. Additionally, the compounds described herein can exist in unsolvated as well as solvated forms with pharmaceutically acceptable solvents such as water, ethanol, and the like. The solvated forms of the compounds presented herein are also considered to be disclosed herein. In addition, the pharmaceutical compositions may include other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions can also contain other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The compositions may be in liquid solutions or suspensions, solid forms suitable for solution or suspension in a liquid prior to use, or as emulsions. These compositions may also contain minor amounts of nontoxic, auxiliary substances, such as wetting or emulsifying agents, pH buffering agents, and so forth.

A summary of pharmaceutical compositions described herein may be found, for example, in *Remington: The Science and Practice of Pharmacy*, Nineteenth Ed (Easton, Pa.: Mack Publishing Company, 1995); Hoover, Jolm E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and* Drug Delivery Systems, Seventh Ed. (Lippincott Williams & Wilkins 1999), herein incorporated by reference in their entirety.

Methods of Administration and Treatment Methods

For convenience, the compositions, uses and methods described in this section and other parts herein use a single formula, such as "Formula (1)," by way of example. However, the compositions, uses and methods described herein apply equally well to all formulas presented herein that fall within the scope of Formula (A), including compounds having the structure of Formula (B), Formula (C), Formula (E), Formula (F), Formula (G), Formula (H), Formula (I), Formula (J), Formula (K), Formula (1), Formula (2), Formula (4), Formula (5), Formula (6), as well as to all of the specific compounds that fall within the scope of these generic formula.

The compounds of Formula (1) can be used in the preparation of medicaments for the treatment of diseases or conditions in which steroid hormone nuclear receptor activity contributes to the pathology and/or symptomology of the disease. In addition, a method for treating any of the diseases or conditions described herein in a subject in need of such treatment, involves administration of pharmaceutical compositions containing at least one compound of Formula (1), or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician. It is considered well within the skill of the art for one to determine such therapeutically effective amounts by routine experimentation (including, but not limited to, a dose escalation clinical trial).

Compositions containing the compound(s) described herein can be used to treat a disease-state or condition selected from: arteriosclerosis, neurological diseases, cancer, Conn's Syndrome, primary and secondary hyperaldosteronism, increased sodium retention, increased magnesium and potassium excretion (diuresis), increased water retention, hypertension (isolated systolic and combined systolic/diastolic), arrhythmias, myocardial fibrosis, myocardial infarction, Barter's Syndrome, congestive heart failure (CHF), conditions associated with excess catecholamine levels, cognitive dysfunctions, psychoses, cognitive conditions, memory disturbances, mood conditions, depression, bipolar condition, anxiety conditions, personality conditions, inflammation, tissue rejection, auto-immunity, malignancies such as leukemias and lymphomas, Cushing's syndrome, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, stroke, spinal cord injury, hypocalcemia, hyperglycemia, chronic primary adrenal insufficiency, secondary adrenal insufficiency, cerebral edema, thrombocytopenia, Little's syndrome, inflammatory bowel disease, systemic lupus erythematosus, polyartitis nodosa, Wegener's granulomatosis, giant cell arthritis, rheumatoid arthritis, osteoarthritis, hay fever, allergic rhinitis, urticaria, angioneurotic edema, chronic obstructive pulmonary disease, asthma, tendonitis, bursitis, Crohn's disease, ulcerative colitis, autoimmune chronic active hepatitis, organ transplantation, hepatitis, cirrhosis; wound healing and tissue repair, inflammatory scalp alopecia, panniculitis, psoriasis, discoid lupus, inflamed cysts, atopic dermatitis, pyoderma gangrenosum, pemphigus vulgaris, bullous pemphigoid, dermatomyositis, eosinophilic fasciitis, relapsing polychondritis, inflammatory vasculitis, sarcoidosis, Sweet's disease, type 1 reactive leprosy, capillary hemangiomas, contact dermatitis, lichen planus, exfoliative dermatitis, erythema nodosum, acne, hirsutism, toxic epidermal necrolysis, erythema multiform, emphysema, neuroinflammatory conditions, multiple sclerosis, Alzheimer's disease, prostate cancer, benign prostatic hyperplasia, alopecia, anorexia nervosa, breast cancer, musculoskeletal conditions, such as bone disease, hematopoietic conditions, neuromuscular disease, rheumatological disease, wasting disease, AIDS, cachexia, for hormone replacement therapy (HRT), employed in male contraception, for male performance enhancement, for male reproductive conditions, primary or secondary male hypogonadism, testicular cancer, ovarian cancer, lung cancer, cardiovascular diseases, neurodegenerative conditions, CNS conditions, GI tract conditions, osteoporosis, bone loss, bone fractures, Paget's disease, abnormally increased bone turnover, periodontal disease, tooth loss, periprosthetic osteolysis, osteogenesis imperfecta, metastatic bone disease, hypercalcemia of malignancy, and multiple myeloma, cartilage degeneration, endometriosis, uterine fibroid disease, uterine cancer, hot flashes, cerebral degenerative conditions, restenosis, gynecomastia, vascular smooth muscle cell proliferation, obesity, incontinence, and, non-malignant chronic conditions, such as fibroids, in a patient in need of such treatment, the method comprising administering to the patient an effective amount of a compound described herein, or a tautomer, prodrug, solvate, or salt thereof.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition. In the case wherein the patient's status does improve, upon the doctor's discretion the administration of the compounds may be given continuously or temporarily suspended for a certain length of time (i.e., a "drug holiday").

Once improvement of the patient's conditions has occurred, a maintenance dose is administered if necessary. Subsequently, the dosage or the frequency of administration, or both, can be reduced, as a function of the symptoms, to a level at which the improved disease or condition is retained. Patients can, however, require intermittent treatment on a long-term basis upon any recurrence of symptoms.

In certain instances, it may be appropriate to administer therapeutically effective amounts of at least one of the compounds described herein (or a pharmaceutically acceptable salts, pharmaceutically acceptable N-oxides, pharmaceutically active metabolites, pharmaceutically acceptable prodrugs, and pharmaceutically acceptable solvates thereof) in combination with another therapeutic agent. By way of example only, if one of the side effects experienced by a patient upon receiving one of the compounds herein is inflammation, then it may be appropriate to administer an anti-inflammatory agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. In any case, regardless of the disease or condition being treated, the overall benefit experienced by the patient may simply be additive of the two therapeutic agents or the patient may experience a synergistic benefit. For example, synergistic effects can occur with compounds of Formula (1) and other substances used in the treatment of hypokalemia, hypertension, congestive heart failure, renal failure, in particular chronic renal failure, restenosis, atherosclerosis, syndrome X, obesity, nephropathy, post-myocardial infarction, coronary heart disease, increased formation of collagen, fibrosis and remodeling following hypertension and endothelial dysfunction. Examples of such compounds include anti-obesity agents, such as orlistat, anti-hypertensive agents, inotropic agents and hypolipidemic agents including, but not limited to, loop diuretics, such as ethacrynic acid, furosemide and torsemide; angiotensin converting enzyme (ACE) inhibitors, such as benazepril, captopril, enalapril, fosinopril, lisinopril, moexipril, perinodopril, quinapril, ramipril and trandolepril; inhibitors of the Na-K-ATPase membrane pump, such as digoxin; neutralendopeptidase (NEP) inhibitors; ACE/NEP inhibitors, such as omapatrilat, sampatrilat, and fasidotril; angiotensin II antagonists, such as candesartan, eprosartan, irbesartan, losartan, telmisartan and valsartan, in particular-valsartan; β-adrenergic receptor blockers, such as acebutolol, betaxolol, bisoprolol, metoprolol, nadolol, propanolol, sotalol and timolol; inotropic agents, such as digoxin, dobutamine and milrinone; calcium channel blockers, such as amlodipine, bepridil, diltiazem, felodipine, nicardipine, nimodipine, nifedipine, nisoldipine and verapamil; and 3-hydroxy-3-methyl-glutaryl coenzyme A reductase (HMG-CoA) inhibitors, such as lovastatin, pitavastatin, simvastatin, pravastatin, cerivastatin, mevastatin, velostatin, fluvastatin, dalvastatin, atorvastatin, rosuvastatin and rivastatin. Where the compounds described herein are administered in conjunction with other therapies, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is one of the compounds described herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; we envision the use of multiple therapeutic combinations In addition, the compounds of Formula (1) may also be used in combination with procedures that may provide additional or synergistic benefit to the patient. By way of example only, patients are expected to find therapeutic and/or prophylactic benefit in the methods described herein, wherein pharmaceutical composition of Formula (1) and/or combinations with other therapeutics are combined with genetic testing to determine whether that individual is a carrier of a mutant gene that is known to be correlated with certain diseases or conditions.

The compounds of Formula (1) and combination therapies can be administered before, during or after the occurrence of a disease or condition, and the timing of administering the composition containing a compound can vary. Thus, for example, the compounds can be used as a prophylactic and can be administered continuously to subjects with a propensity to conditions or diseases in order to prevent the occurrence of the disease or condition. The compounds and compositions can be administered to a subject during or as soon as possible after the onset of the symptoms. The administration of the compounds can be initiated within the first 48 hours of the onset of the symptoms, preferably within the first 48 hours of the onset of the symptoms, more preferably within the first 6 hours of the onset of the symptoms, and most preferably within 3 hours of the onset of the symptoms. The initial administration can be via any route practical, such as, for example, an intravenous injection, a bolus injection, infusion over 5 minutes to about 5 hours, a pill, a capsule, transdermal patch, buccal delivery, and the like, or combination thereof. A compound is preferably administered as soon as is practicable after the onset of a disease or condition is detected or suspected, and for a length of time necessary for the treatment of the disease, such as, for example, from about 1 month to about 3 months. The length of treatment can vary for each subject, and the length can be determined using the known criteria. For example, the compound or a formulation containing the compound can be administered for at least 2 weeks, preferably about 1 month to about 5 years, and more preferably from about 1 month to about 3 years.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The daily dosages appropriate for the compounds of Formula (1) described herein are from about 0.03 to 2.5 mg/kg per body weight. An indicated daily dosage in the larger mammal, including, but not limited to, humans, is in the range from about 0.5 mg to about 100 mg, conveniently administered in divided doses, including, but not limited to, up to four times a day or in retard form. Suitable unit dosage forms for oral administration comprise from about 1 to 50 mg active ingredient. The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, for determining the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Kits/Articles of Manufacture

For use in the therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers can be formed from a variety of materials such as glass or plastic.

For example, the container(s) can comprise one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically may comprise one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

ILLUSTRATIVE EXAMPLES

The following examples provide illustrative methods for making and testing the effectiveness and safety of the compounds of Formula (A). These examples are provided for illustrative purposes only and not to limit the scope of the claims provided herein. All of the methods disclosed and claimed herein can be made and executed without undue experimentation in light of the present disclosure. It will be apparent to those of skill in the art that variations may be applied to the methods and in the steps or in the sequence of steps of the method described herein without departing from the concept, spirit and scope of the claims. All such similar substitutes and modifications apparent to those skilled in the art are deemed to be within the spirit, scope and concept of the appended claims.

Example 1

Synthesis of Dibenzosuberenone Compounds

Example 1a

Synthesis of Trimethylsilyl-Cyano Dibenzosuberenone Compound

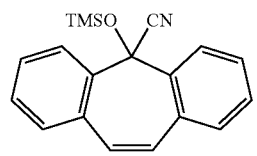

The dibenzosuberenone compound can be synthesized by the following procedure. To a stirred solution of 5H-Dibenzo[a,d]cyclohepten-5-One (10 g, 48 mmol) and iodine (5 mol %) in dichloromethane (DCM) (60 mL), TMSCN (8.0 mL, 60 mmol) is added slowly at 0° C. and the mixture allowed to stir at room temperature for 1 hour. The reaction is quenched with saturated sodium thiosulfate ($Na_2S_2O_3$) solution and most of the DCM removed. The residue is extracted with ethyl acetate (EtOAc) and the aqueous layer separated. The organic layer is washed with brine, dried over magnesium sulfate ($MgSO_4$) and filtered. The filtrate is concentrated in vacuo and the crude dibenzosuberone compound 2a compound is used in the next step without purification.

Example 1b

Synthesis of Amino-Alcohol Dibenzosuberenone Compound (3a)

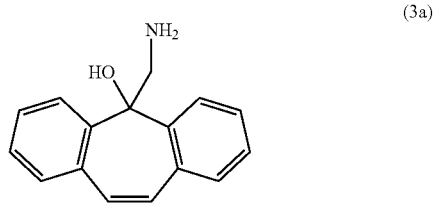

(3a)

Under $N_2$, $LiAlH_4$ (1M in THF; 60 mL, 60 mmol) is added slowly to a solution of the trimethylsilyl-cyano dibenzosuberenone compound (48 mmol) in THF (80 mL) at 0° C. The mixture is stirred at room temperature for 0.5 hours then at 40° C. for additional 4 hours. The mixture is cooled and quenched carefully with EtOAc (~10 mL) then with 2M NaOH solution until white solid precipitates out. The white solid is filtered and washed thoroughly with EtOAc. The filtrate is concentrated in vacuo to remove most of the DCM and the residue extracted with EtOAc. The aqueous layer is separated and the organic layer washed with brine, dried over $MgSO_4$ and filtered. The filtrate is concentrated in vacuo and the crude title compound is used in the next step without purification. Spectral data for 3•HCl. $^1$H NMR (400 MHz, DMSO-$d_6$) 2.95 (s, 2H), 7.04 (s, 2H), 7.25-7.35 (m, 2H), 7.35-7.48 (m, 4H), 7.89 (d, 2H, J=8.0 Hz); MS (ESI) m/z 220 [M−OH]$^+$.

Example 2

Synthesis of Dibenzosuberone Compounds

Example 2a

Synthesis of Trimethylsilyl-Cyano Dibenzosuberone Compound

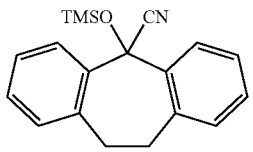

The dibenzosuberone compound can be synthesized by the following procedure. To a stirred solution of 10,11-dihydro-5H-Dibenzo[a,d]cyclohepten-5-One (4.1 g, 19.7 mmol) and iodine (5 mol %) in DCM (60 mL), TMSCN (2.7 mL, 20 mmol) is added slowly at 0° C. and the mixture stirred at 90° C. for 12 hours. The reaction mixture is cooled, quenched with saturated $Na_2S_2O_3$ solution and most of the DCM removed. The residue is extracted with EtOAc and the aqueous layer separated. The organic layer is washed with brine, dried over $MgSO_4$ and filtered. The filtrate is concentrated in vacuo and the crude product purified by flash chromatography on silica gel (hexane/EtOAc=15/1) to afford the title compound as a colorless syrup.

Example 2b

Synthesis of Amino-Alcohol Dibenzosuberenone Compound (3b)

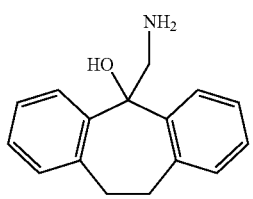

(3b)

Under $N_2$, $LiAlH_4$ (1M in THF; 60 mL, 60 mmol) is added slowly to a solution of the trimethylsilyl-cyano dibenzosuberone compound (48 mmol) in THF (80 mL) at 0° C. The mixture is stirred at room temperature for 0.5 hours then at 40° C. for additional 4 hours. The mixture is cooled and quenched carefully with EtOAc (~10 mL) then with 2M NaOH solution until white solid precipitates out. The white solid is filtered and washed thoroughly with EtOAc. The filtrate is concentrated in vacuo to remove most of the DCM and the residue extracted with EtOAc. The aqueous layer is separated and the organic layer washed with brine, dried over $MgSO_4$ and filtered. The filtrate is concentrated in vacuo and the crude title compound is used in the next step without purification. Spectral data for 3•HCl. $^1$H NMR (400 MHz, DMSO-$d_6$) 2.95 (s, 2H), 7.04 (s, 2H), 7.25-7.35 (m, 2H), 7.35-7.48 (m, 4H), 7.89 (d, 2H, J=8.0 Hz); MS (ESI) m/z 220 [M–OH]$^+$.

Example 3

Synthesis of Fused-ring Spiro Compounds

Fused-ring spiro compounds can be obtained by cyclocondensation of a ketoacid with amino-alcohol intermediates, such as compounds 3a or 3b, in a suitable refluxing solvent using a Dean-Stark trap (see scheme 7 and scheme 8). In general, a solution of a starting intermediate, such as compounds 3a or 3b, (HCl salt, 1.0 mol equiv) and a ketoacid (1.0-1.5 mol equiv) in toluene (25 ml) are refluxed using the Dean-Stark apparatus, with the progress of the reaction being monitored by analytical TLC until completion within about 8 to 12 hours. After cooling to room temperature the toluene is removed and the crude product purified. Fused-ring spiro-dibenzosuberenone compounds FRS-1 through FRS-14 are synthesized according to scheme 7 and scheme 8, as described below.

Example 3a

Synthesis of Compound FRS-1

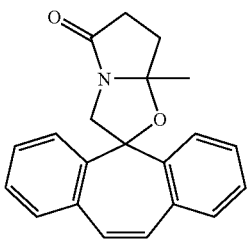

FRS-1

Compound FRS-1 is prepared from compound 3a (1.1 g, 4.8 mmol) and 4—Oxo-pentanoic acid (0.5 mL, 4.9 mmol) according to scheme 7 and scheme 8. The crude product is triturated in hexane-diethyl ether ($Et_2O$) (4:1 v/v) and the solid filtered to afford the title compound as a white solid: $^1$H NMR (400 MHz, CDCl$_3$) 1.54 (s, 3H), 2.28-2.46 (m, 2H), 2.54-2.64 (m, 1H), 2.67-2.77 (m, 1H), 3.13 (dd, 1H, J=12.0, 0.8 Hz), 4.59 (d, 1H, J=12.4 Hz), 7.05 (d, 1H, J=11.6 Hz), 7.10 (d, 1H, J=11.6 Hz), 7.16-7.40 (m, 6H), 7.74 (d, 1H, J=7.6 Hz), 7.87 (d, 1H, J=8.0 Hz); MS (ESI) m/z 318 [M+H]$^+$. Chirally pure FRS-1 is obtained by synthesis using chiral HPLC using the following conditions: Column and Dimensions: Whelk-01 10/100 25 cm×4.6 mm ID, flow Rate: 1 mL/min, sample concentration: 1 mg/mL dissolved in MeOH, sample Run Time: 45 minutes, solvent conditions: 30% Isopropanol and 70% Hexanes wavelength monitored: 220 nm.

Example 3b

Synthesis of Compound FRS-2

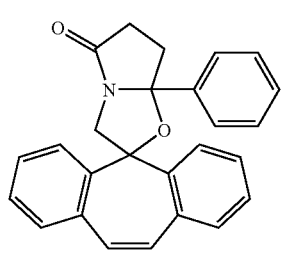

FRS-2

Compound FRS-2 is prepared from compound 3a (0.5 g, 2.1 mmol) and 4—Oxo-4-phenyl-butyric acid (0.38 g, 2.1 mmol) according to scheme 7 and scheme 8. The crude product is triturated in $Et_2O$ and the solid filtered to afford the title compound as a white solid: MS (ESI) m/z 380 [M+H]$^+$.

Example 3c

Synthesis of Compound FRS-3

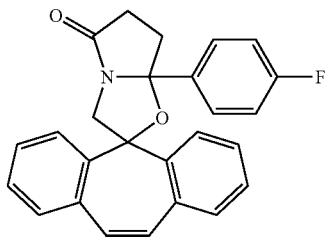

FRS-3

Compound FRS-3 is prepared from compound 6a (0.5 g, 2.1 mmol) and 4-(4-fluoro-phenyl)-4—Oxo-butyric acid (0.4 g, 2.1 mmol) according to scheme 7 and scheme 8. The crude product is triturated in Et$_2$O and the solid filtered to afford the title compound as a white solid: MS (ESI) m/z 398 [M+H]$^+$.

Example 3d

Synthesis of Compound FRS-4

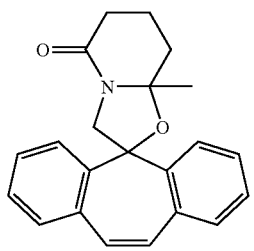

FRS-4

Compound FRS-4 is prepared from compound 3a (0.66 g, 2.8 mmol) and 5—Oxo-hexanoic acid (0.35 mL, 2.9 mmol) according to scheme 7 and scheme 8. The crude product is purified by flash chromatography on silica gel (hexane/EtOAc=3/2) to afford the title compound as a white solid: MS (ESI) m/z 332 [M+H]$^+$.

Example 3e

Synthesis of Compound FRS-5

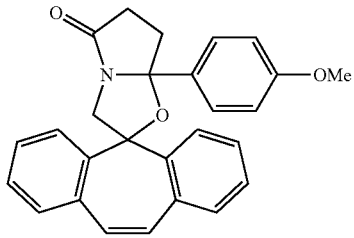

FRS-5

Compound FRS-5 is prepared from compound 3a (0.2 g, 0.73 mmol) and 4-(4-methoxy-phenyl)-4—Oxo-butyric acid (0.16 g, 0.77 mmol) according to scheme 7 and scheme 8. The crude product is triturated in Et$_2$O and the solid filtered to afford the title compound as a white solid: MS (ESI) m/z 410 [M+H]$^+$.

Example 3f

Synthesis of Compound FRS-6

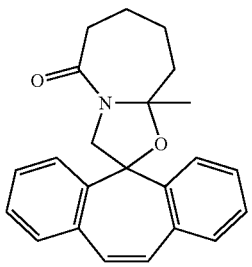

FRS-6

Compound FRS-6 is prepared from compound 3a (0.1 g, 0.37 mmol) and 6—Oxo-heptanoic acid (55 mg, 0.38 mmol) according to scheme 7 and scheme 8. The crude product is purified by HPLC (10% CH$_3$CN/water to 90% CH$_3$CN/water in 7 min) to afford the title compound as a white solid: MS (ESI) m/z 346 [M+H]$^+$.

Example 3g

Synthesis of Compound FRS-7

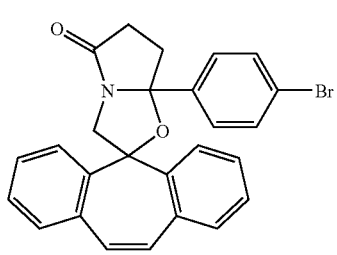

FRS-7

Compound FRS-7 is prepared from compound 3a (0.1 g, 0.37 mmol) and 4-(4-bromo-phenyl)-4—Oxo-butyric acid (95 mg, 0.37 mmol) according to scheme 7 and scheme 8. The crude product is triturated in hexane-Et$_2$O (4:1 v/v) and the solid filtered to afford the title compound as a white solid: MS (ESI) m/z 459 [M+H]$^+$.

Example 3h

Synthesis of Compound FRS-8

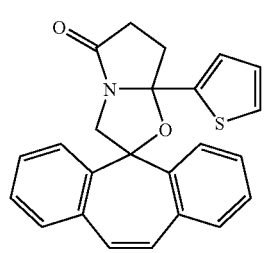

FRS-8

Compound FRS-8 is prepared from compound 3a (0.3 g, 1.1 mmol) and 4—Oxo-4-thiophen-2-yl-butyric acid (0.21 g, 1.1 mmol) according to scheme 7 and scheme 8. The residue is triturated in Et$_2$O and the solid filtered. The filtrate is concentrated and the crude product purified by flash chromatography on silica gel (hexane/EtOAc=8/2) to afford the title compound as a white solid: MS (ES) m/z 386 [M+H]$^+$.

Example 3i

Synthesis of Compound FRS-9

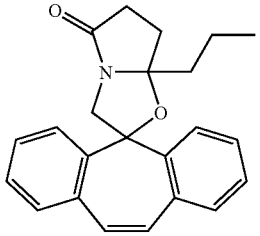

FRS-9

Compound FRS-9 is prepared from compound 3a (0.1 g, 0.37 mmol) and 4—Oxo-heptanoic acid (53 mg, 0.37 mmol) according to scheme 7 and scheme 8. The crude product is triturated in hexane-Et$_2$O (5:1 v/v) and the solid filtered to afford the title compound as an off white solid: MS (ESI) m/z 346 [M+H]$^+$.

Example 3j

Synthesis of Compound FRS-10

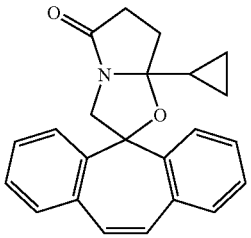

FRS-10

Compound FRS-10 is prepared from compound 3a (1.1 g, 4.8 mmol) and 4—Oxo-4-cyclopropyl-2-yl-butyric acid (0.5 mL, 4.9 mmol) according to scheme 7 and scheme 8. The crude product is purified by HPLC (10% CH$_3$CN/water to 90% CH$_3$CN/water in 7 min) to afford the title compound as a white solid: MS (ESI) m/z 344 [M+H]$^+$.

Example 3k

Synthesis of Compound FRS-1

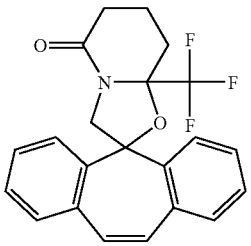

FRS-11

Compound FRS-11 is prepared from compound 3a (250 mg, 0.91 mmol) and 4—Oxo-4-trifluoromethyl-2-yl-butyric acid (0.1 mL, 0.92 mmol) according to scheme 7 and scheme 8. The crude product is purified by HPLC (10% CH$_3$CN/water to 90% CH$_3$CN/water in 7 minutes) to afford the title compound as a white solid: MS (ESI) m/z 386 [M+H]$^+$.

Example 3l

Synthesis of Compound FRS-12

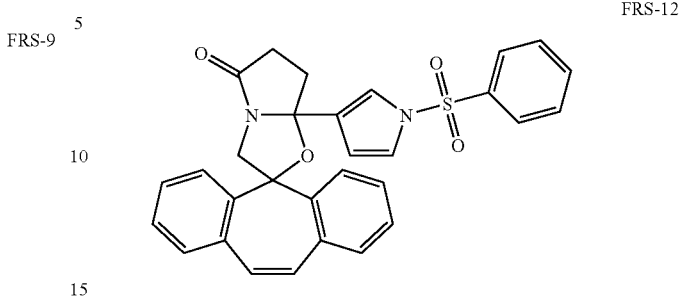

FRS-12

Compound FRS-12 is prepared from compound 3a (237 mg, 0.8 mmol) and 4—Oxo-4-[3-(N-phenylsulfonyl)pyrrole]-2-yl-butyric acid (0.1 mL, 1 mmol) according to scheme 7 and scheme 8. The crude product purified by HPLC (10% CH$_3$CN/water to 90% CH$_3$CN/water in 7 min) to afford the title compound as a white solid: MS (ESI) m/z 509 [M+H]$^+$.

Example 3m

Synthesis of Compound FSR-13

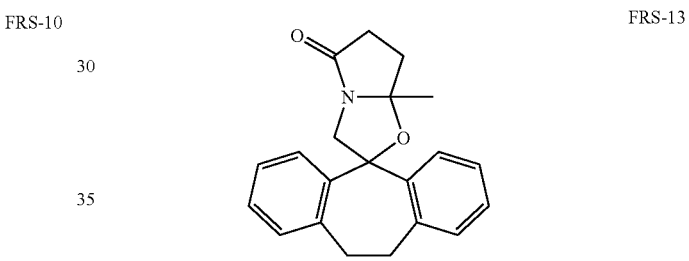

FRS-13

Compound FRS-13 is prepared from compound 3b (0.7 g, 2.9 mmol) and 4—Oxo-pentanoic acid (0.3 mL, 2.9 mmol) according to scheme 7 and scheme 8. The crude product is triturated in hexane-Et$_2$O (4:1 v/v) and the solid filtered to afford the title compound as a white solid: MS (ESI) m/z 320 [M+H]$^+$. Chirally pure FRS-13 is obtained by synthesis using chiral HPLC using the following conditions: Column and Dimensions: Whelk-01 10/100 25 cm×4.6 mm ID, flow Rate: 1 mL/min, sample concentration: 1 mg/mL dissolved in MeOH, sample Run Time: 45 minutes, solvent conditions: 30% Isopropanol and 70% Hexane wavelength monitored: 220 nm

Example 3n

Synthesis of Compound FSR-14

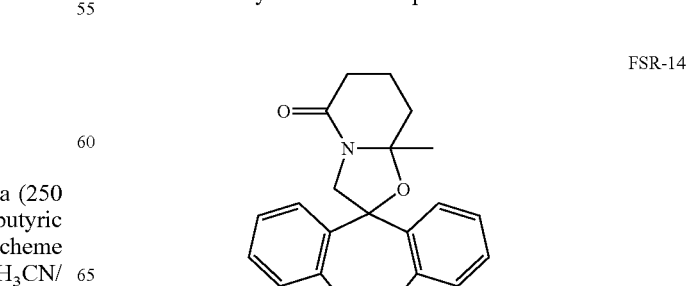

FSR-14

Compound FSR-14 is prepared from compound 3b (0.7 g, 2.9 mmol) and 5—Oxo-hexanoic acid (0.35 mL, 2.9 mmol) according to scheme 7 and scheme 8. The crude product is triturated in hexane-Et$_2$O (4:1 v/v) and the solid filtered to afford the title compound as an off white solid: MS (ESI) m/z 334 [M+H]$^+$.

Example 4

Synthesis of Oxazoline Spiro Compounds

Oxazoline spiro-compounds of Formula (G) may be synthesized by reaction of amino-alcohol compounds of Formula (D) with imidate compounds according to Scheme 9. In addition, oxazoline spiro-dibenzosuberenone, or oxazoline spiro-dibenzosuberone compounds, of Formula (6) may be synthesized by reaction of amino-alcohol compounds (3a) or (3b), respectively, with imidate compounds according Scheme 10. By way of example, synthesis of oxazoline spiro-dibenzosuberenone compounds OXS-1 through OXS-3 is described below.

Example 4a

Synthesis of Compound OXS-1

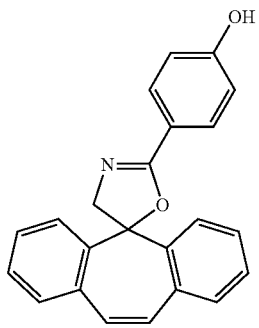

OXS-1

A solution of a compound 3a (0.1 g, 0.37 mmol) and 4-hydroxy-benzimidic acid ethyl ester hydrochloride (75 mg, 0.37 mmol) in a mixture of toluene-DMF (4:1 v/v, 5 mL) is stirred at 80° C. for 12 hours. After cooling to room temperature, the mixture is concentrated. The crude product is triturated in hexane-Et$_2$O (4:1 v/v) and the solid filtered to afford the title compound as a white solid: $^1$H NMR (400 MHz, DMSO-d$_6$) 3.98 (s, 2H), 6.94 (d, 2H, J=8.8 Hz), 7.18 (s, 2H), 7.30-7.37 (m, 2H), 7.40-7.45 (m, 2H), 7.50 (d, 2H, J=7.6 Hz), 7.75 (d, 2H, J=8.0 Hz), 8.01 (d, 2H, J=8.8 Hz), 10.2 (s, 1H); MS (ESI) m/z 340 [M+H]$^+$.

Example 4b

Synthesis of Compound OXS-2

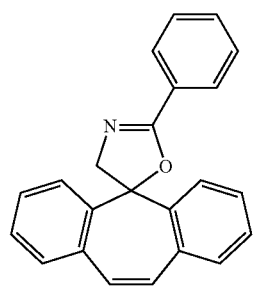

OXS-2

A solution of a compound 3a (0.1 g, 0.37 mmol) and benzimidic acid ethyl ester hydrochloride (0.37 mmol) in a mixture of toluene-DMF (4:1 v/v, 5 mL) is stirred at 80° C. for 12 h. After cooling to room temperature, the mixture is concentrated. The crude product is triturated in hexane-Et$_2$O (4:1 v/v) and the solid filtered to afford the title compound as a white solid: MS (ESI) m/z 324 [M+H]$^+$.

Example 4c

Synthesis of Compound OXS-3

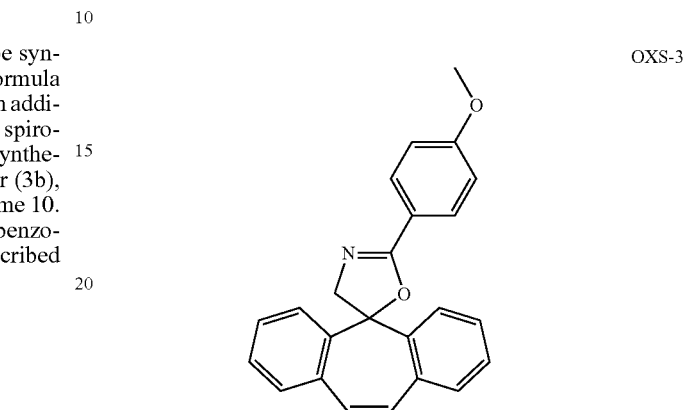

OXS-3

A solution of a compound 3a (0.1 g, 0.37 mmol) and 4-methoxybenzimidic acid ethyl ester hydrochloride (0.37 mmol) in a mixture of toluene-DMF (4:1 v/v, 5 mL) is stirred at 80° C. for 12 h. After cooling to room temperature, the mixture is concentrated. The crude product is triturated in hexane-Et$_2$O (4:1 v/v) and the solid filtered to afford the title compound as a white solid: MS (ESI) m/z 354 [M+H]$^+$.

Example 5

Synthesis of Oxazolidine Spiro Compounds

Oxazolidine spiro-compounds of Formula (E) may be synthesized by reaction of amino-alcohol compounds of Formula (D) with ketone compounds according to Scheme 11. In addition, oxazolidine spiro-dibenzosuberenone, or oxazolidine spiro-dibenzosuberone compounds, of Formula (4) may be synthesized by reaction of amino-alcohol compounds (3a) or (3b), respectively, with ketone compounds according Scheme 12. By way of example, synthesis of oxazolidine spiro-dibenzosuberenone compounds BOXS-1 and BOXS-2 is described below.

Example 5a

Synthesis of Compound BOXS-1

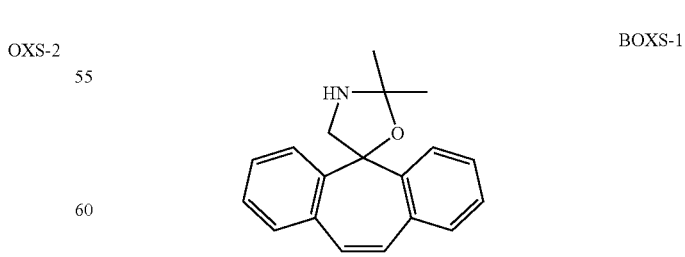

BOXS-1

Compound BOXS-1 is prepared from compound 3a; wherein a solution of compound 3a (1.0 g, 3.7 mmol) in acetone (20 mL) is heated at reflux for 12 h. The resulting solution is cooled and the solvent removed. The residue is triturated in hexane and the solid filtered. The filtrate is concentrated and the crude product purified by flash chromatography on silica gel (hexane/EtOAc=7/3) to afford the title compound as a white solid: $^1$H NMR (600 MHz, CDCl$_3$) 1.55 (s, 6H), 3.53 (s, 2H), 7.01 (s, 2H), 7.22-7.25 (m, 2H), 7.32 (d, 2H, J=5.0 Hz), 7.34-7.38 (m, 2H), 7.93 (d, 2H, J=5.3 Hz); MS (ESI) m/z 278 [M+H]$^+$.

Example 5b

Synthesis of Compound BOXS-2

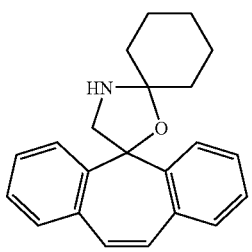

BOXS-2

Compound BOXS-2 is prepared from compound 3a; wherein to a solution of compound 3a (0.55 g, 2.3 mmol) in 1,2-dichloroethane (10 mL) is added cyclohexanone (4.0 mL, 39 mmol) and TsOH (5 mol %). The mixture is heated at 80° C. for 12 h. The resulting mixture is cooled and the solvent removed. The crude product is purified by flash chromatography on silica gel (hexane to hexane/EtOAc=8/2) to afford the title compound as a pale yellow solid: $^1$H NMR (400 MHz, CDCl$_3$) 1.40-1.95 (m, 10H), 3.37 (s, 2H), 7.00 (s, 2H), 7.20-7.26 (m, 2H), 7.29-7.39 (m, 4H), 7.97 (d, 2H, J=8.0 Hz); MS (ESI) m/z 318 [M+H]$^+$.

Example 5c

Synthesis of Compound BOXS-3

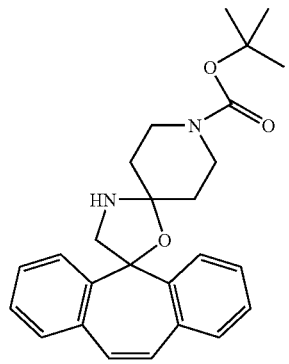

BOXS-3

Compound BOXS-3 is prepared as described for BOXS-2. MS (ES$^+$) 460, m/z (M+23) 483.

Example 6

Synthesis of Substituted Oxazolidine Spiro Compounds

Substituted oxazolidine Spiro-compounds of Formula (F) may be synthesized by reaction of oxazolidine Spiro-compounds of Formula (E) with an electrophilic reactant according to Scheme 11. In addition, substituted oxazolidine spiro-dibenzosuberenone, or substituted oxazolidine spiro-dibenzosuberone compounds, of Formula (5) may be synthesized by reaction of oxazolidine spiro-compounds of Formula (4), with an electrophilic reactant according Scheme 12. By way of example, synthesis of substituted oxazolidine spiro-dibenzosuberenone compounds SOXS-1 to SOXS-6 is described below.

Example 6a

Synthesis of Compound SOXS-1

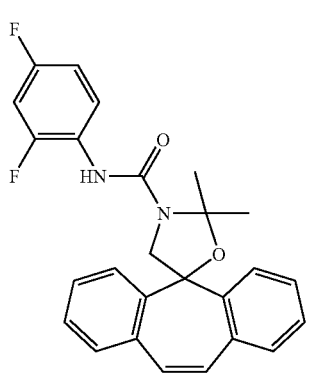

SOXS-1

Compound SOXS-1 is prepared from a solution of a compound BOXS-1 (50 mg, 0.18 mmol) and 2,4-difluorophenyl isocyanate (0.02 mL, 0.18 mmol) in DCM (4 mL) which is stirred at room temperature for 2 hours. The resulting mixture is concentrated and the residue triturated in hexane. The solid is filtered to afford the title compound as a white solid: 1.84 (s, 6H), 3.94 (s, 2H), 5.98 (s, 1H), 6.78 (m, 2H), 7.11 (s, 2H), 7.29 (dd, J=7.6, 1.2 Hz, 2H), 7.72 (dd, J=8.0, 1.6 Hz, 2H), 7.6 (m, 2H), 7.84 (m, 1H), 7.98 (dd, J=8.0, 1.2 Hz, 2H). MS (ES) m/z 433 [M+H]$^+$.

Example 6b

Synthesis of Compound SOXS-2

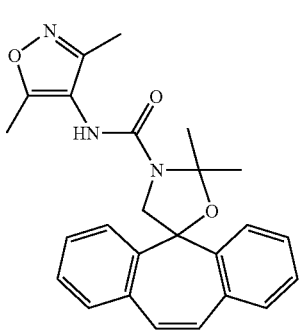

SOXS-2

Compound SOXS-2 is synthesized from a solution of a compound BOXS-1 (30 mg, 0.16 mmol) and 3,5-dimethylisoxazole isocyanate (0.02 mL, 0.18 mmol) in DCM (4 mL) which is stirred at room temperature for 2 hours. After removal of the solvents under reduced pressure, the crude product is purified by HPLC (10% CH₃CN/water to 90% CH₃CN/water in 7 min) to afford the title compound as a white solid: MS (ESI) m/z 456 [M+H]⁺.

Example 6c

Synthesis of Compound SOXS-3

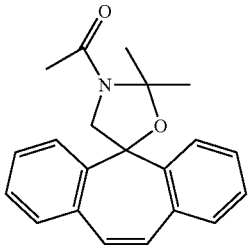

SOXS-3

Compound SOXS-3 is synthesized from a solution of a compound BOXS-1, wherein to a solution of a compound BOXS-1 (50.0 mg, 0.18 mmol) in dichloromethane (2 ml) and N,N-diisopropyl amine (0.2 ml) is added acetyl chloride (0.015 ml, 0.3 mmol) at room temperature. The mixture is stirred at RT for 2 h, diluted with EtOAc and washed with saturated aqueous Na₂CO₃ and brine, then dried over MgSO₄. After removal of the solvents under reduced pressure, the crude product is purified by flash chromatography on silica gel (hexane to hexane/EtOAc=8/2) to afford the title compound (50.0 mg, 0.156 mmol, yield: 87%) as a white solid: MS (ESI) m/z 320 [M+H]⁺.

Example 6d

Synthesis of Compound SOXS-4

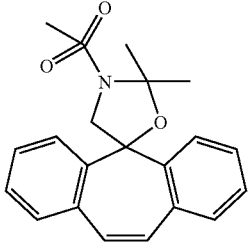

SOXS-4

Compound SOXS-4 is synthesized from a solution of a compound BOXS-1, wherein to a solution of a compound BOXS-1 (50.0 mg, 0.18 mmol) in dichloromethane (2 ml) and N,N-diisopropyl amine (0.2 ml) is added methanesulfonyl chloride (0.015 ml, 0.3 mmol) at room temperature. The mixture is stirred at room temperature for 2 hours, diluted with EtOAc and washed with saturated aqueous Na₂CO₃ and brine, then dried over MgSO₄. After removal of the solvents under reduced pressure, the crude product is purified by flash chromatography on silica gel (hexane to hexane/EtOAc=8/2) to afford the title compound as a white solid: MS (ESI) m/z 356 [M+H]⁺.

Example 6e

Synthesis of Compound SOXS-5

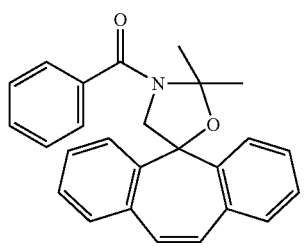

SOXS-5

Compound SOXS-5 is synthesized from a solution of a compound BOXS-1; wherein to a solution of a compound BOXS-1 (50.0 mg, 0.18 mmol) in dichloromethane (2 ml) and N,N-diisopropyl amine (0.2 ml) is added benzoyl chloride (0.02 ml, 0.3 mmol) at room temperature. The mixture is stirred at room temperature for 2 hours, diluted with EtOAc and washed with saturated aqueous Na₂CO₃ and brine, then dried over MgSO₄. After removal of the solvents under reduced pressure, the crude product is purified by flash chromatography on silica gel (hexane to hexane/EtOAc=8/2) to afford the title compound as a white solid: MS (ESI) m/z 382 [M+H]⁺.

Example 6f

Synthesis of Compound SOXS-6

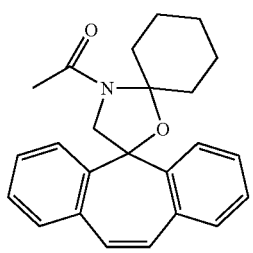

SOXS-6

Compound SOXS-6 is synthesized from a solution of a compound BOXS-2; wherein to a solution of a compound BOXS-2 (50.0 mg, 0.18 mmol) in dichloromethane (2 ml) and N,N-diisopropyl amine (0.2 ml) is added acetyl chloride (0.01 ml, 0.3 mmol) at room temperature. The mixture is stirred at room temperature for 2 hours, diluted with EtOAc and washed with saturated aqueous Na₂CO₃ and brine, then dried over MgSO₄. After removal of the solvents under reduced pressure, the crude product is purified by flash chromatography on silica gel (hexane to hexane/EtOAc=8/2) to afford the title compound as a white solid: MS (ESI) m/z 360 [M+H]⁺.

Example 6g

Synthesis of Compound SOXS-7

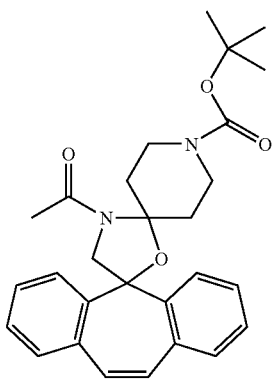

Compound SOXS-7 is synthesized from a solution of a compound BOXS-3 as described for the synthesis of SOXS-6.

Example 7

Pharmaceutical Compositions

Example 7a

Parenteral Composition

To prepare a parenteral pharmaceutical composition suitable for administration by injection, 100 mg of a water-soluble salt of a compound of Formula (1) is dissolved in DMSO and then mixed with 10 mL of 0.9% sterile saline. The mixture is incorporated into a dosage unit form suitable for administration by injection.

Example 7b

Oral Composition

To prepare a pharmaceutical composition for oral delivery, 100 mg of a compound of Formula (1) is mixed with 750 mg of lactose. The mixture is incorporated into an oral dosage unit for, such as a hard gelatin capsule, which is suitable for oral administration.

Example 8

Functional Assay of Mineralocorticoid Receptor Antagonism

The MR antagonist activity of the compounds is determined in a mammalian two hybrid reporter system. The N-terminus of MR (MR-NT, sequence coding amino acid 1-597) is fused to the activation domain of the VP16 gene. The ligand binding domain of MR (MR-LBD, sequence encoding amino acid 672-984) is fused to the DNA binding domain of the yeast Gal4 gene. The MR gene is cloned from a human kidney cDNA library with PCR.

The assay is performed in 384 well plates. Briefly, 293T cells (ATCC) are transfected with expression vectors for Gal-4-MR-LBD and VP16-MR NT, and a luciferase reporter vector containing Gal4 binding sequence (pG5-Luc). Cells are plated in 384 well plates immediately after transfection (approximately $3 \times 10^4$ cells/well in 50 µl medium). The medium is supplemented with 3% charcoal-dextran treated fetal bovine serum (Hyclone). Twenty four hours after transfection, compounds prepared in DMSO are transferred to the cells. The cells are then stimulated with 0.4 nM final concentration of aldosterone (Acros) and incubated at 37° C. for another 24 hours before the luciferase activity is assayed with 20 µl of Bright-Glo (Promega) using a luminometer (CLIPR). The expression of luciferase is used as an indicator of aldosterone-induced MR trans-activation. Each compound is tested in duplicates with 12-concentration titration. $IC_{50}$ values (defined as the concentration of test compound required to antagonize 50% of aldosterone-induced MR activity) are determined from the dose-response curve.

Example 9

Functional Assay of Glucocorticoid Receptor Antagonism

The GR antagonist activity of the compounds is determined in a mammalian two hybrid reporter system. The ligand binding domain of GR (GR-LBD, sequence encoding amino acid 541-778) is fused to the DNA binding domain of the yeast Gal4 gene. The GR gene is cloned from a human lung cDNA library with PCR.

The assay is performed in 384 well plates: COS-7 cells (ATCC) are transfected with expression vectors for Gal-4-GR-LBD and a luciferase reporter vector containing Gal4 binding sequence (pG5-Luc). Cells are plated in 384 well plates immediately after transfection (approximately 8000 cells/well in 50 µl medium). The medium is supplemented with 3% charcoal-dextran treated fetal bovine serum (Hyclone). Twenty four hours after transfection, compounds prepared in DMSO are transferred to the cells. The cells are then stimulated with 10 nM final concentration of dexamethasone (Sigma) and incubated at 37° C. for another 24 hours before the luciferase activity is assayed with 20 µl of Bright-Glo (Promega) using a luminometer (CLIPR). The expression of luciferase is used as an indicator of dexamethasone-induced GR trans-activation. Each compound is tested in duplicates with a 12-concentration titration. $IC_{50}$ values (defined as the concentration of test compound required to antagonize 50% of dexamethasone-induced GR activity) are determined from the dose-response curve.

Example 10

Functional Assay of Progesterone Receptor Antagonism

The PR antagonist activity of the compounds is determined by progesterone-induced alkaline phosphatase activity in the T-47D cell line (ATCC). In the T-47D breast cancer cells, progesterone specifically induces de novo synthesis of a membrane-associated alkaline phosphatase enzyme in a time and dose-dependent manner (Di Lorenzo et al., Cancer Research, 51: 4470-4475 (1991)). The alkaline phosphatase enzymatic activity can be measured with a chemiluminescent substrate, such as CSPD® (Applied Biosystems).

The assay is performed in 384 well plates. Briefly, T-47D cells are plated in 384 well plates at a density of approximately $2.5 \times 10^4$ cells/well in 50 µl medium supplemented with 10% fetal bovine serum. Twenty four hours later, the medium is aspirated. New medium that is free of phenol red and serum is added to the cells. Compounds prepared in DMSO are transferred to the cells. The cells are then stimulated with 3 nM final concentration of progesterone (Sigma) and incubated at 37° C. for another 24 hours before the alkaline phosphatase is assayed with 25 µl of CSPD® (Applied Biosystems) using a luminometer (CLIPR). The expression of alkaline phosphatase is used as an indicator of progesterone-induced PR trans-activation. Each compound is tested in duplicates with a 12-concentration titration. $IC_{50}$ values (defined as the concentration of test compound required to antagonize 50% of progesterone-induced PR activity) are determined from the dose-response curve.

Example 11

Functional Assay of Androgen Receptor Antagonism

The AR antagonist activity of the compounds is determined with the MDA-Kb2 cell line (ATCC), which stably expresses the MMTV luciferase reporter. The MMTV promoter is a mouse mammary tumor virus promoter that contains androgen receptor response elements. The MDA-kb2 cells is derived from the MDA-MB-453 cells, which has been shown to express high levels of functional, endogenous androgen receptor (Wilson et al., Toxicological Sciences, 66: 69-81 (2002)). Upon stimulation with AR ligands, such as dihydrotestosterone, the MMTV luciferase reporter can be activated.

The assay is performed in 384 well plates. Briefly, MDA-kb2 cells are plated in 384 well plates at a density of approximately $2.4 \times 10^4$ cells/well in 50 µl medium. The medium is supplemented with 5% charcoal-dextran treated fetal bovine serum (Hyclone). Twenty four hours later, compounds prepared in DMSO are transferred to the cells. The cells are then stimulated with 0.3 nM final concentration of dihydrotestosterone (Sigma) and incubated at 37° C. for another 24 hours before the luciferase activity is assayed with 20 µl of Bright-Glo (Promega) using a luminometer (CLIPR). The expression of luciferase is used as an indicator of dihydrotestosterone-induced AR trans-activation. Each compound is tested in duplicates with a 12-concentration titration. $IC_{50}$ values (defined as the concentration of test compound required to antagonize 50% of dihydrotestosterone-induced AR activity) are determined from the dose-response curve.

Exemplary test compounds were evaluated using the functional assays described above for the different steroid hormone nuclear receptors. The ability of exemplary test compounds to antagonize 50% of the specified steroid hormone nuclear receptor is shown in Table 2 as a range of $IC_{50}$ values.

TABLE 2

Ranges of $IC_{50}$ values for test compounds required to antagonize 50% of the specified steroid hormone nuclear receptor.

| Compound | Gal4-MR $IC_{50}$ (µM) | PR-T47D $IC_{50}$ (µM) | MDA-AR $IC_{50}$ (µM) | Gal4-GR $IC_{50}$ (µM) |
|---|---|---|---|---|
| FRS-1 | D | A | C | A |
| FRS-2 | C | A | C | A |
| FRS-3 | C | A | B | A |
| FRS-4 | C | B | A | A |
| FRS-5 | C | A | A | A |
| FRS-6 | C | A | B | A |
| FRS-7 | D | | | |
| FRS-8 | D | B | C | B |
| FRS-9 | D | B | C | B |
| FRS-10 | D | A | C | B |
| FRS-11 | D | A | C | B |

TABLE 2-continued

Ranges of $IC_{50}$ values for test compounds required to antagonize 50% of the specified steroid hormone nuclear receptor.

| Compound | Gal4-MR $IC_{50}$ (µM) | PR-T47D $IC_{50}$ (µM) | MDA-AR $IC_{50}$ (µM) | Gal4-GR $IC_{50}$ (µM) |
|---|---|---|---|---|
| FRS-12 | C | | | |
| FRS-13 | D | A | C | A |
| FRS-14 | C | B | B | A |
| FRS-1 (Chiral Synthesis) | D | A | C | B |
| FRS-13 (Chiral Synthesis) | D | A | C | A |
| OXS-1 | C | A | B | A |
| OXS-2 | C | | | |
| OXS-3 | C | | | |
| SOXS-1 | B | B | A | A |
| SOXS-2 | C | | | |
| SOXS-3 | C | B | B | B |
| SOXS-4 | D | C | B | A |
| SOXS-5 | C | | | |
| SOXS-6 | C | C | B | A |

A = >10
B = 1-10
C = 0.1-1
D = <0.1

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A compound having the structure of Formula (1):

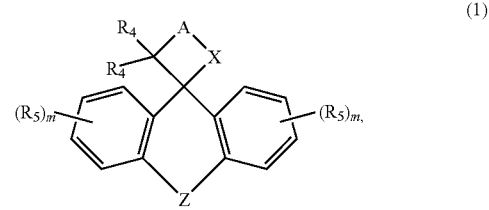

(1)

wherein,
(a) A is $NR_1$—$CR_2R_3$ or N=$CR_2$; X is O; Z is $CR_6$=$CR_6$ or $C(R_6)_2$—$C(R_6)_2$;
(b) $R_1$ is H, or an optionally substituted moiety selected from -$L_1$-alkyl, -$L_1$-cycloalkyl, -$L_1$-heteroalkyl, -$L_1$-haloalkyl, -$L_1$-aryl, -$L_1$-heterocycloalkyl, and -$L_1$-heteroaryl, wherein $L_1$ is selected from a bond, —C(O)—, —C(S)—, —C(O)O—, —C(O)NH—, —S(O)—, —S(O)$_2$, and —S(O)NH—; wherein said optional substituents of an $R_1$ moiety are selected from halogen, OH, $C_{1-6}$alkyl, $C_{1-6}$alkoxy, halo-$C_{1-6}$alkyl and halo-$C_{1-6}$alkoxy;

$R_2$ and $R_3$ are independently selected from H, halogen, $NH_2$, SH, $NO_2$, CN, and an optionally substituted moiety selected from -$L_2$-alkyl, -$L_2$-cycloalkyl, -$L_2$-heteroalkyl, -$L_2$-haloalkyl, -$L_2$-aryl, -$L_2$-heterocycloalkyl, and -$L_2$-heteroaryl, wherein $L_2$ is selected from a bond, O, NH, S, —C(O)—, —C(S)—, —C(O)O—, —C(O)NH—, —S(O)—, —S(O)$_2$—, and —S(O)NH—; wherein said optional substituents of an $R_2$ or $R_3$ moiety are selected from halogen, OH, —S(O)$_2$-phenyl, $C_{1-6}$alkyl, $C_{1-6}$alkoxy, halo-$C_{1-6}$alkyl and halo-$C_{1-6}$alkoxy; or $R_1$ and $R_2$ together form an optionally substituted 3 to 8-membered heterocyclic ring; or $R_2$ and $R_3$ together form an optionally substituted 3 to 8-membered cycloalkyl, carbocyclic or heterocyclic ring;

(c) each $R_4$ is independently selected from H, halogen, OH, $NH_2$, SH, $NO_2$, CN, and an optionally substituted moiety selected from -$L_2$-alkyl, -$L_2$-cycloalkyl, -$L_2$-heteroalkyl, -$L_2$-haloalkyl, -$L_2$-aryl, -$L_2$-heterocycloalkyl, and -$L_2$-heteroaryl, wherein $L_2$ is selected from a bond, O, NH, S, —C(O)—, —C(S)—, —C(O)O—, —C(O)NH—, —S(O)—, —S(O)$_2$, and —S(O)NH—;

(d) each $R_5$ is independently selected from halogen, OH, $NH_2$, SH, $NO_2$, CN, and an optionally substituted moiety selected from -$L_2$-alkyl, -$L_2$-cycloalkyl, -$L_2$-heteroalkyl, -$L_2$-haloalkyl, -$L_2$-aryl, -$L_2$-heterocycloalkyl, and -$L_2$-heteroaryl, wherein $L_2$ is selected from a bond, O, NH, S, —C(O)—, —C(S)—, —C(O)O—, —C(O)NH—, —S(O)—, —S(O)$_2$, and —S(O)NH—, and wherein each m is independently selected from 0, 1, 2, 3, 4, and 5;

(e) each $R_6$ is independently selected from H, halogen, OH, $NH_2$, SH, $NO_2$, CN, and an optionally substituted moiety selected from -$L_2$-alkyl, -$L_2$-cycloalkyl, -$L_2$-heteroalkyl, -$L_2$-haloalkyl, -$L_2$-aryl, -$L_2$-heterocycloalkyl, and -$L_2$-heteroaryl, wherein $L_2$ is selected from a bond, O, NH, S, —C(O)—, —C(S)—, —C(O)O—, —C(O)NH—, —S(O)—, —S(O)$_2$, and —S(O)NH—, or any two $R_6$ groups can together form a 3 to 8-membered carbocyclic or heterocyclic ring; and (f) each $R_7$ and $R_8$ is independently selected from H and ($C_1$-$C_4$)alkyl; and a pharmaceutically acceptable salt, or pharmaceutically acceptable N-oxide thereof.

2. The compound of claim 1, wherein Z is $CR_6$=$CR_6$.

3. The compound of claim 1, wherein Z is $C(R_6)_2$—$C(R_6)_2$.

4. The compound of claim 1, wherein A is $NR_1$—$CR_2R_3$.

5. The compound of claim 4, wherein Z is $CR_6$=$CR_6$.

6. The compound of claim 4, wherein Z is $C(R_6)_2$—$C(R_6)_2$.

7. The compound of claim 4, wherein $R_1$ and $R_2$ together form a 3 to 8-membered heterocyclic ring.

8. The compound of claim 7, having the structure of Formula (2):

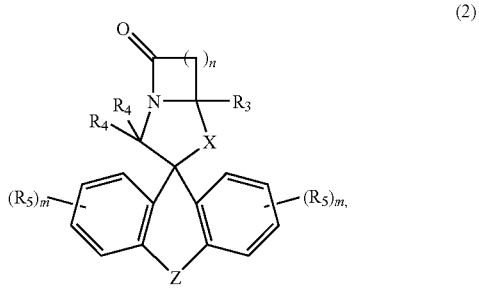

(2)

wherein n is 0, 1, 2, 3, 4 or 5.

9. The compound of claim 8, wherein Z is $CR_6$=$CR_6$.

10. The compound of claim 8, wherein Z is $C(R_6)_2$—$C(R_6)_2$.

11. The compound of claim 4, wherein $R_1$ is — an optionally substituted moiety selected from -$L_1$-alkyl, -$L_1$-cycloalkyl, -$L_1$-heteroalkyl, -$L_1$-haloalkyl, -$L_1$-aryl, -$L_1$-heterocycloalkyl, and -$L_1$-heteroaryl, wherein $L_1$ is selected from a bond, —C(O)—, —C(S)—, —C(O)O—, —C(O)NH—, —S(O)—, —S(O)$_2$, and —S(O)NH—; wherein said optional substituents of an $R_1$ moiety are selected from halogen, OH, $C_{1-6}$alkyl, $C_1$-6alkoxy, halo-$C_{1-6}$alkyl and halo-$C_{1-6}$alkoxy.

12. The compound of claim 4, wherein $R_2$ and $R_3$ together form an optionally substituted 3 to 8-membered cycloalkyl, carbocyclic or heterocyclic ring.

13. The compound of claim 12, wherein Z is $CR_6$=$CR_6$.

14. The compound of claim 12, wherein Z is $C(R_6)_2$—$C(R_6)_2$.

15. The compound of claim 12, wherein $R_1$ is an optionally substituted moiety selected from -$L_1$-alkyl, -$L_1$-cycloalkyl, -$L_1$-heteroalkyl, -$L_1$-haloalkyl, -$L_1$-aryl, -$L_1$-heterocycloalkyl, and -$L_1$-heteroaryl, wherein $L_1$ is selected from a bond, —C(O)—, —C(S)—, —C(O)O—, —C(O)NH—, —S(O)—, —S(O)$_2$, and —S(O)NH—; wherein said optional substituents of an $R_1$ moiety are selected from halogen, OH, $C_{1-6}$alkyl, $C_{1-6}$alkoxy, halo-$C_{1-6}$alkyl and halo-$C_{1-6}$alkoxy.

16. The compound of claim 1, wherein A is N=$CR_2$.

17. The compound of claim 16, wherein Z is $CR_6$=$CR_6$.

18. The compound of claim 16, wherein Z is $C(R_6)_2$—$C(R_6)_2$.

19. A pharmaceutical composition comprising at least one compound having the structure of Formula (1);

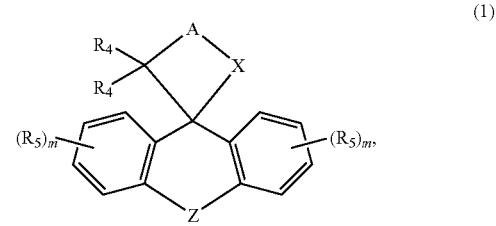

(1)

wherein, (a) A is $NR_1$—$CR_2R_3$ or N=$CR_2$; X is O; Z is $CR_6$=$CR_6$ or $C(R_6)_2$—$C(R_6)_2$;

(b) $R_1$ is H, or an optionally substituted moiety selected from -$L_1$-alkyl, -$L_1$-cycloalkyl, -$L_1$-heteroalkyl, -$L_1$-haloalkyl, -$L_1$-aryl, -$L_1$-heterocycloalkyl, and -$L_1$-heteroaryl, wherein $L_1$ is selected from a bond, —C(O)—, —C(S)—, —C(O)O—, —C(O)NH—, —S(O)—, —S(O)$_2$, and —S(O)NH—; wherein said optional substituents of an $R_1$ moiety are selected from halogen, OH, $C_{1-6}$alkyl, $C_{1-6}$alkoxy, halo-$C_{1-6}$alkyl and halo-$C_{1-6}$alkoxy;

$R_2$ and $R_3$ are independently selected from H, halogen, —$NH_2$, SH, $NO_2$, CN and an optionally substituted moiety selected from -$L_2$-alkyl, -$L_2$-cycloalkyl, -$L_2$-heteroalkyl, -$L_2$-haloalkyl, -$L_2$-aryl, -$L_2$-heterocycloalkyl, and -$L_2$-heteroaryl, wherein $L_2$ is selected from a bond, O, NH, S, —C(O)—, —C(S)—, —C(O)O—, —C(O)NH—, —S(O)—, —S(O)$_2$—, and —S(O)NH—; wherein said optional substituents of an $R_2$ or $R_3$ moiety are selected from halogen, OH, —S(O)$_2$-phenyl, $C_{1-6}$alkyl, $C_{1-6}$alkoxy, halo-$C_{1-6}$alkyl and halo-$C_{1-6}$alkoxy; or $R_1$ and $R_2$ together form an optionally substituted 3 to 8-membered heterocyclic ring; or $R_2$ and $R_3$ together form an optionally substituted 3 to 8-membered cycloalkyl, carbocyclic or heterocyclic ring;

(c) each $R_4$ is independently selected from H, halogen, OH, $NH_2$, SH, $NO_2$, CN, and an optionally substituted moiety selected from -$L_2$-alkyl, -$L_2$-cycloalkyl, -$L_2$-heteroalkyl, $L_2$-haloalkyl, $L_2$-aryl, $L_2$-heterocycloalkyl, and -$L_2$-heteroaryl, wherein $L_2$ is selected from a bond, O, NH, S, —C(O)—, —C(S)— —C(O)O—, —C(O)NH—, —S(O)—, —S(O)$_2$, and —S(O)NH—;

(d) each $R_5$ is independently selected from halogen, OH, $NH_2$, SH, $NO_2$, CN, and an optionally substituted moiety selected from -$L_2$-alkyl, -$L_2$-cycloalkyl, -$L_2$-heteroalkyl, $L_2$ haloalkyl, $L_2$ aryl, -$L_2$-heterocycloalkyl, and -$L_2$-heteroaryl, wherein $L_2$ is selected from a bond, O, NH, S, —C(O)—, —C(S)— —C(O)O—, —C(O)NH—, —S(O)—, —S(O)$_2$, and —S(O)NH—, and wherein each m is independently selected from 0, 1, 2, 3, 4, and 5;

(e) each $R_6$ is independently selected from H, halogen, OH, $NH_2$, SH, $NO_2$, CN, and an optionally substituted moiety selected from -$L_2$-alkyl, -$L_2$-cycloalkyl, -$L_2$-heteroalkyl, $L_2$-haloalkyl, $L_2$-aryl, $L_2$-heterocycloalkyl, and -$L_2$-heteroaryl, wherein $L_2$ is selected from a bond, O, NH, S, —C(O)—, —C(S)— —C(O)O—, —C(O)NH—, —S(O)—, —S(O)$_2$, and —S(O)NH—, or any two $R_6$ groups can together form a 3 to 8-membered carbocyclic or heterocyclic ring; and (f) each $R_7$ and $R_8$ is independently selected from H and ($C_1$-$C_4$)alkyl, or a pharmaceutically acceptable salt, or pharmaceutically acceptable N-oxide thereof, in admixture with one or more suitable excipients.

20. The pharmaceutical composition of claim 19, wherein the one or more excipients are suitable for parenteral administration.

21. The pharmaceutical composition of claim 19, wherein the one or more excipients are suitable for oral administration.

22. The pharmaceutical composition of claim 19, wherein the one or more excipients are suitable for ophthalmic administration.

23. A compound of claim 1 selected from:

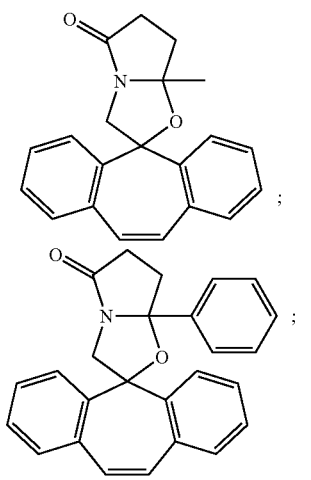

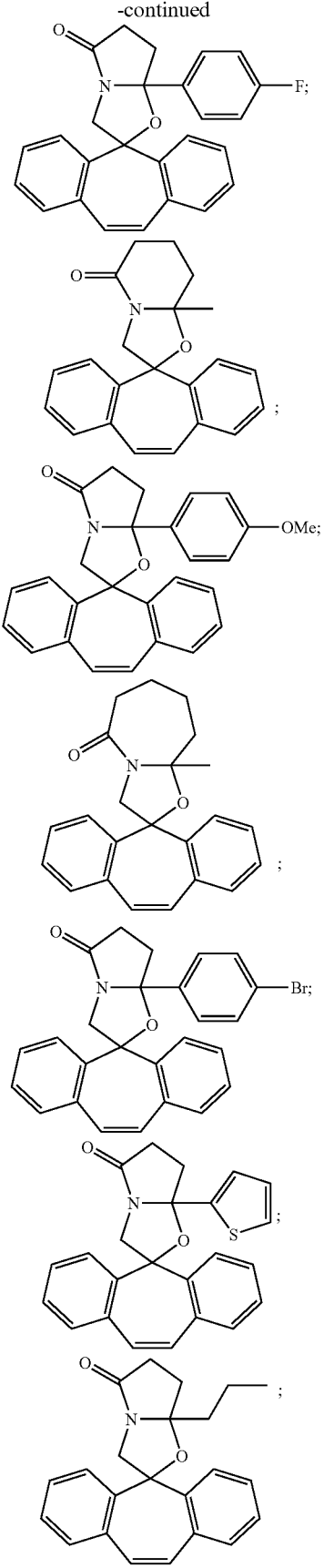

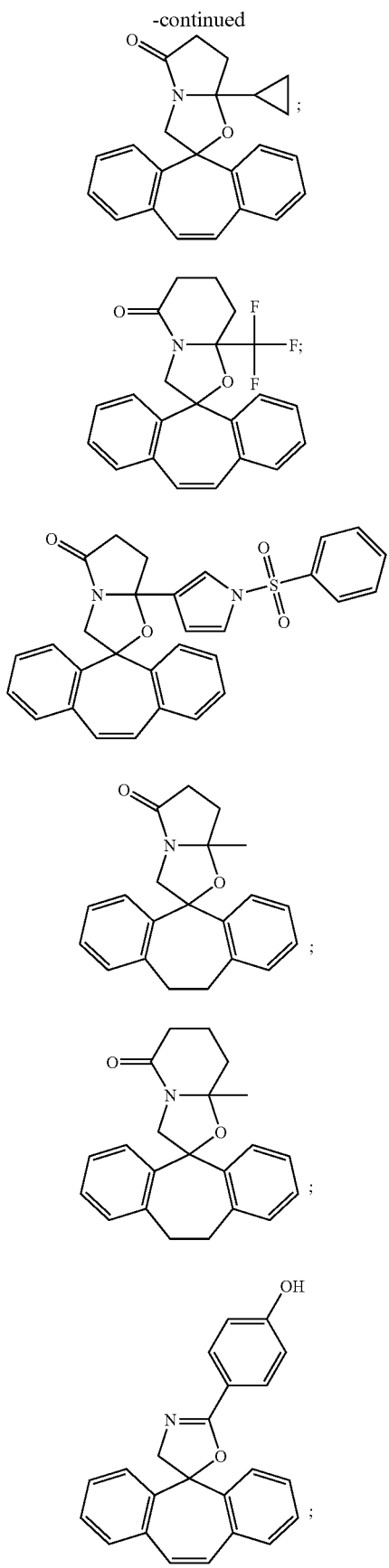
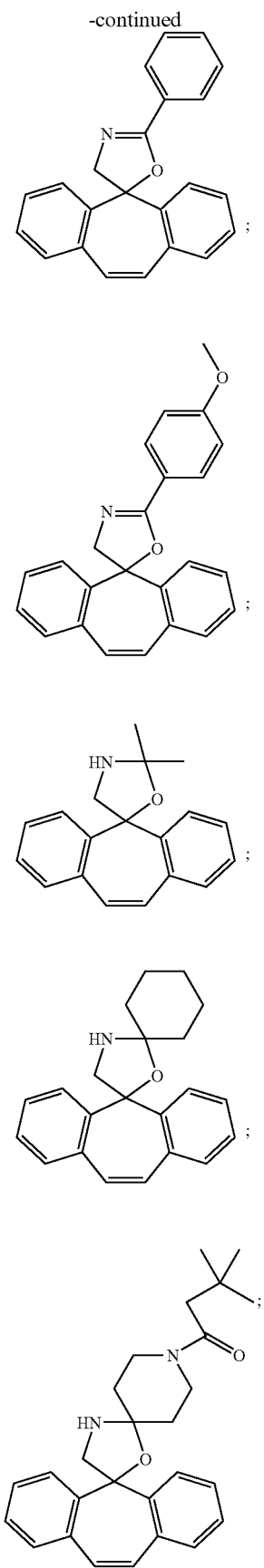

-continued
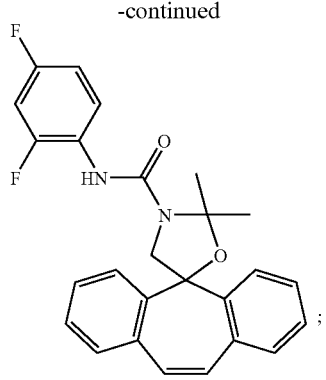
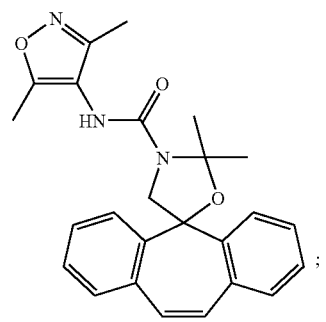
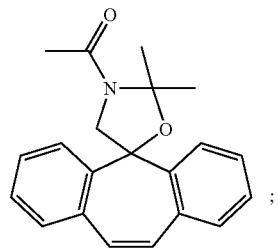
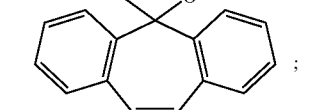
-continued
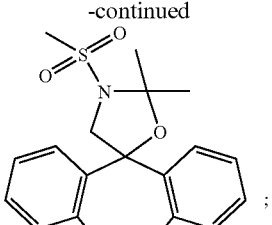
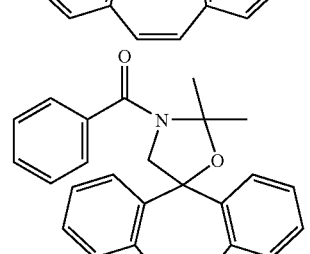
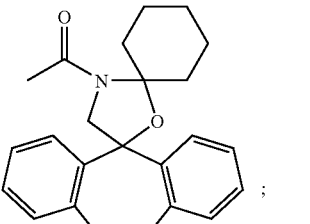
and
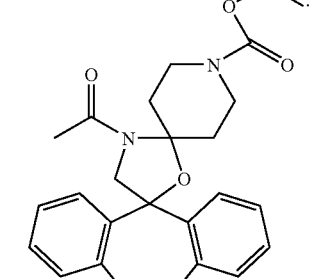
* * * * *